(12) United States Patent
Caterina et al.

(10) Patent No.: US 12,311,236 B1
(45) Date of Patent: *May 27, 2025

(54) METHOD AND SYSTEM UTILIZING IMAGING ANALYSIS FOR GOLF BALLS

(71) Applicant: Topgolf Callaway Brands Corp., Carlsbad, CA (US)

(72) Inventors: Julie Caterina, Carlsbad, CA (US); Megan Ilnicky, Chicopee, MA (US)

(73) Assignee: Topgolf Callaway Brands Corp., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,349

(22) Filed: Feb. 16, 2024

Related U.S. Application Data

(63) Continuation of application No. 18/114,431, filed on Feb. 27, 2023, now Pat. No. 11,904,214, which is a continuation of application No. 17/347,185, filed on Jun. 14, 2021, now Pat. No. 11,590,394, which is a continuation of application No. 17/178,159, filed on Feb. 17, 2021, now Pat. No. 11,058,924.

(60) Provisional application No. 62/978,686, filed on Feb. 19, 2020, provisional application No. 63/084,388, filed on Sep. 28, 2020.

(51) Int. Cl.
*A63B 47/00* (2006.01)
*A63B 37/00* (2006.01)
*G01N 23/04* (2018.01)
*G01N 23/083* (2018.01)
*G01N 23/18* (2018.01)

(52) U.S. Cl.
CPC ........... *A63B 47/008* (2013.01); *G01N 23/04* (2013.01); *G01N 23/083* (2013.01); *G01N 23/18* (2013.01); *A63B 37/0076* (2013.01); *A63B 2225/055* (2013.01); *G01N 2223/401* (2013.01); *G01N 2223/646* (2013.01)

(58) Field of Classification Search
CPC .............. A63B 47/008; A63B 37/0076; A63B 2225/055; G01N 23/04; G01N 23/083; G01N 23/18; G01N 2223/401; G01N 2223/646

See application file for complete search history.

(56) References Cited

U.S. PATENT DOCUMENTS

| | | | |
|---|---|---|---|
| 11,058,924 B1 * | 7/2021 | Caterina | G01N 23/04 |
| 11,590,394 B1 * | 2/2023 | Caterina | G01N 23/18 |
| 11,904,214 B1 * | 2/2024 | Caterina | G01N 33/008 |
| 11,911,666 B1 * | 2/2024 | Ilnicky | A63B 37/0029 |
| 11,911,667 B1 * | 2/2024 | Ilnicky | A63B 47/008 |

* cited by examiner

*Primary Examiner* — Courtney D Thomas
(74) *Attorney, Agent, or Firm* — Michael A. Catania

(57) ABSTRACT

A method and system for determining concentricity of a multiple layer golf ball are disclosed herein. One or more images of a golf ball are generated using an X-ray source, a camera or a digital detector, and an image intensifier. An edge detection algorithm is preferably utilized. The method also includes calculating Y,Z center coordinates of the a best fit diameter or ellipse of the inner edge layer and outer edge layer of the multiple layer golf ball.

5 Claims, 29 Drawing Sheets

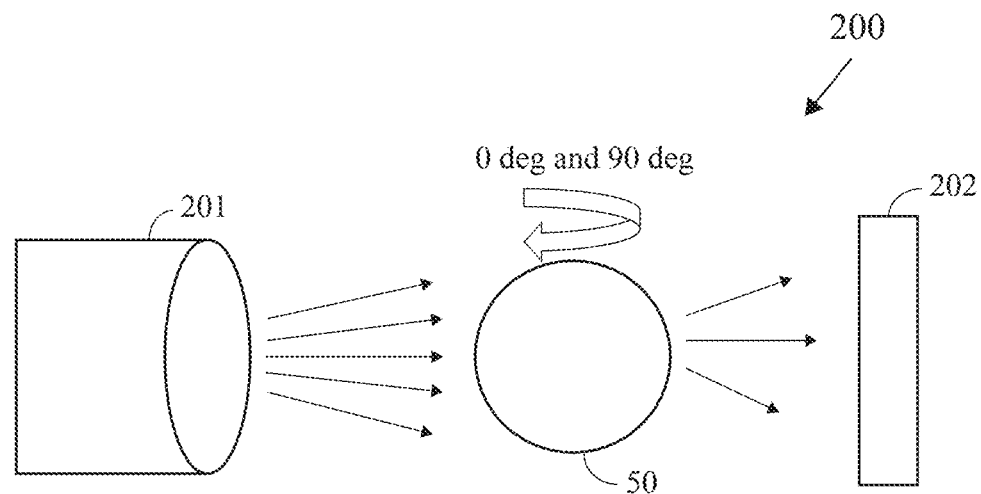
FIG. 2
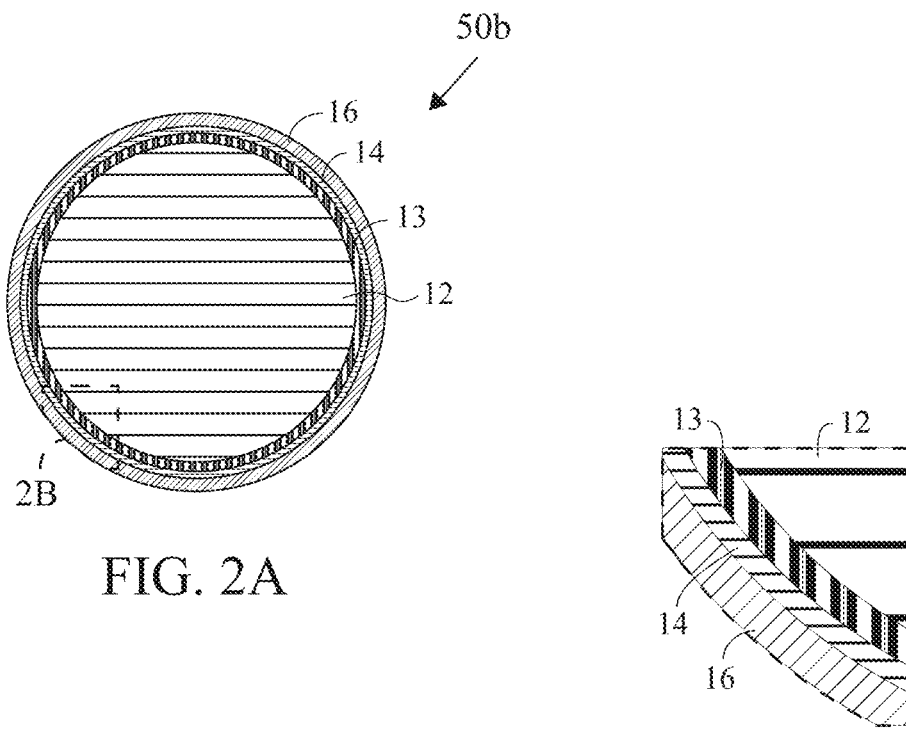
FIG. 2A
FIG. 2B

INNER EDGE

METHOD AND SYSTEM UTILIZING IMAGING ANALYSIS FOR GOLF BALLS

CROSS REFERENCES TO RELATED APPLICATIONS

The Present Application is a continuation application of U.S. patent application Ser. No. 18/114,431, filed on Feb. 27, 2023, which is a continuation application of U.S. patent application Ser. No. 17/347,185, filed on Jun. 14, 2021, now U.S. Pat. No. 11,590,394, issued on Feb. 28, 2023, which is a continuation application of U.S. patent application Ser. No. 17/178,159, filed on Feb. 17, 2021, now U.S. Pat. No. 11,058,924, issued on Jul. 13, 2021, which claims priority to claims priority to U.S. Provisional Patent Application No. 62/978,686, filed on Feb. 19, 2020, and U.S. Provisional Patent Application No. 63/084,388, filed on Sep. 28, 2020, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention relates to a method and system for image scanning a golf ball.

Description of the Related Art

X-ray scanning has been used in the past for golf balls.
Marshall et al., U.S. Pat. No. 6,390,937 for a Method For Verifying The Concentricity Of A Multiple-Layer Golf Ball discloses using an X-ray imaging machine to determine the thickness at various locations of a golf ball to ensure concentricity of the golf ball.

BRIEF SUMMARY OF THE INVENTION

The present invention is a method and system for image scanning a golf ball.

One aspect of the present invention is a method for determining concentricity of a multiple layer golf ball. The method includes positioning a golf ball in an x-ray measurement region of an imaging machine. The method also includes taking one or more images of the golf ball using an x-ray source, camera and image intensifier. The method also includes determining a diameter or ellipse dimensions of an inner edge and an outer edge of a specific layer of the multiple layer golf ball utilizing an edge detection algorithm. The method also includes calculating Y,Z center coordinates of the a best fit diameter or ellipse of the inner edge layer and outer edge layer of the multiple layer golf ball. The method also includes comparing the Y,Z center coordinates of the specific layer to determine concentricity of the inner layer within any of the outer layers.

Another aspect of the present invention is a method for determining concentricity of a multiple layer golf ball. The method includes positioning a golf ball in an x-ray measurement region of an imaging machine. The method also includes taking a plurality of images of the golf ball using an x-ray source and a digital detector. The method also includes averaging the plurality of images into a single image. The method also includes determining a diameter or ellipse dimensions of an inner edge and an outer edge of a layer of the multiple layer golf ball utilizing an edge detection algorithm. The method also includes calculating Y,Z coordinates of the a best fit diameter or ellipse of the inner edge and outer edge the layer of the multiple layer golf ball.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 2 is an illustration of an X-ray scanning apparatus.
FIG. 2A is an X-ray of a golf ball.
FIG. 2B is an isolated view of a portion of an X-ray of a golf ball.

DETAILED DESCRIPTION OF THE INVENTION

A method and system for X-ray image analysis are illustrated in FIGS. 1-10.

Figure 1:
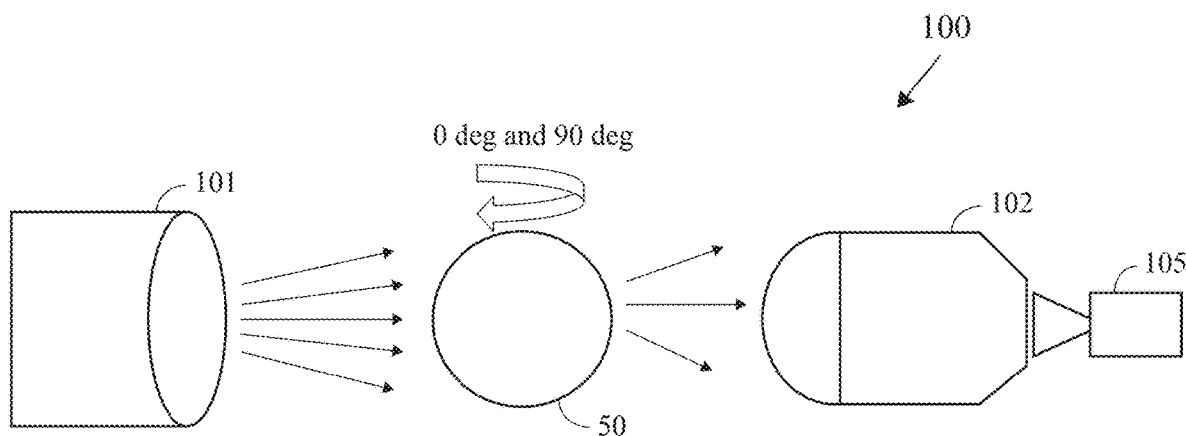
FIG. 1 is an illustration of an X-ray scanning apparatus.
Figure 1A:
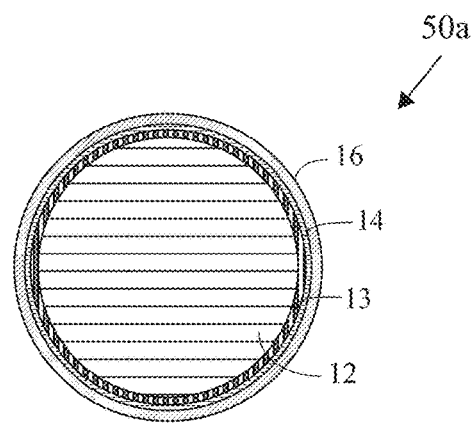
FIG. 1A is an X-ray of a golf ball.

As shown in FIG. 1, an X ray system generally comprises a single source X-ray 101, an image intensifier 102 and camera 105. A golf ball 50 is rotated ninety degrees about an axis. The image intensifier 103 converts X-ray photons into highly visible light at sufficient intensity to provide a viewable image. As shown in FIG. 1A, an X-ray image of a golf ball 50a shows a core 12, an inner mantle layer 13, an outer mantle layer 14 and a cover 16. The X-ray source is preferably a HAMAMATSU L9181-02 X-ray source with a general range of 90-120 kilo-Volts and 40-70 micro-Amps (µAmps). In one example, a 4-piece single core golf ball example, 120 kilo-Volts with 40 micro-Amps are used. Preferably a small focal spot mode is used which equals 5 micro-meters (µm) at 4 watts. A maximum capability is 130 kilo-Volts and 300 µAmps. A preferred camera/intensifier is a HAMAMATSU X-ray image intensifier digital camera unit C7336 series, which includes an image intensifier and a 2.8 megapixel CMOS image sensor.

As shown in FIG. 2, an X-ray system 200 generally comprises a single source X-ray 201 and digital detector 202. A golf ball 50 is rotated ninety degrees about an axis. As shown in FIGS. 2A and 2B, an X-ray image of a golf ball 50b shows a core 12, an inner mantle layer 13, an outer mantle layer 14 and a cover 16. The digital detector 202 uses X-ray sensitive plates to directly capture photons and convert them into an image. Digital detectors 202 generally have better resolution and less distortion error (parallax) but often cost more than their analog equivalent. By using a digital detector 202, a full ball image is obtained showing all layers with high resolution and good contrast. This increased magnification enables one to look at the full ball instead of a local region with a decreased field of view that is required with the analog system. The digital detector 202 is preferably a VAREX 1515DXT-1 X-ray digital detector with a general range of 200-250 milliseconds for exposure and 2-8 images averaged, with a pixel size of 127 µm, a pixel matrix of 1152×1152, and a resolution of 0.00146 inch/pixel (calculated resolution using 1.682" golf ball occupying all 1152 pole pixels×1152 seam pixels). In one example, a 4-piece single core golf ball example, there is an exposure of 250 milliseconds, 2 images averaged, a pixel size of 127 µm, a pixel matrix of 1152×1152, and a resolution of 0.00157 inch/pixel. The sample throughput is preferably 7 seconds per sample time. The golf balls are preferably X-rayed at zero and ninety degrees. Concentricity offsets for a4-piece single core golf ball are calculated for cover to outer mantle, outer mantle to inner mantle, and inner mantle to core, with the results displayed in HMI.

A steady feed of samples can be loaded into the measurement area using an angled rail system. The loading area is directly below the measurement region. The sample is picked up with a robot having a suction cup and is moved directly upwards (vertically) into the X-Ray measurement region in front of the X-Ray source. The sample is held in the measurement location either by the suction cup or placed onto a static fixture for the measurement to be taken. After the measurement the sample will be moved into the appropriate sorting chute and released.

Image intensifier and camera take multiple images (1-24 for analog, 1-8 for digital). Preferably, multiple images are taken and averaged to a single image. An edge detection method is used to determine diameter, or ellipse dimensions, of the inner and outer edges of desired layers. Y,Z coordinates of the best fit diameter or ellipse of the inner and outer edges are calculated.

The sample is then rotated 90 degrees by any of the methods below: having a ball held by a suction cup attached to a robot that rotates 90 degrees; placing a ball on a static fixture for image 1, then picking it up and rotating it and placing it back down for image 2; placing a ball on a static fixture for image 1, static fixture rotates 90 degrees and then image 2 is taken.

Multiple images (1-24 for analog, 1-8 for digital) are taken in the new orientation. An edge detection method is used to determine diameter, or ellipse dimensions, of the inner and outer edges. X,Z coordinates of the best fit diameter or ellipse of the inner and outer edges are calculated. Y,Z and X,Z images are combined to calculate 3D distance of the elliptical centerpoints. The concentricity of the inner and outer edges are calculated using Euclidean distances (3D distance between the center of inner sphere or ellipsoid and outer sphere or ellipsoid). Samples are evaluated against input criteria and sorted based on the criteria, objects will be moved into the appropriate sorting chute and released. The next sample is picked up and presented in front of the X-ray source to repeat the process. Multiple layers can be analyzed with a single set of images (1-24 for analog, 1-8 for digital) as long as the adjacent layers have a visual contrast in the image. This can be achieved by creating different layer densities and/or using different filler materials to create the different X-ray imaging contrast.

Figure 3:
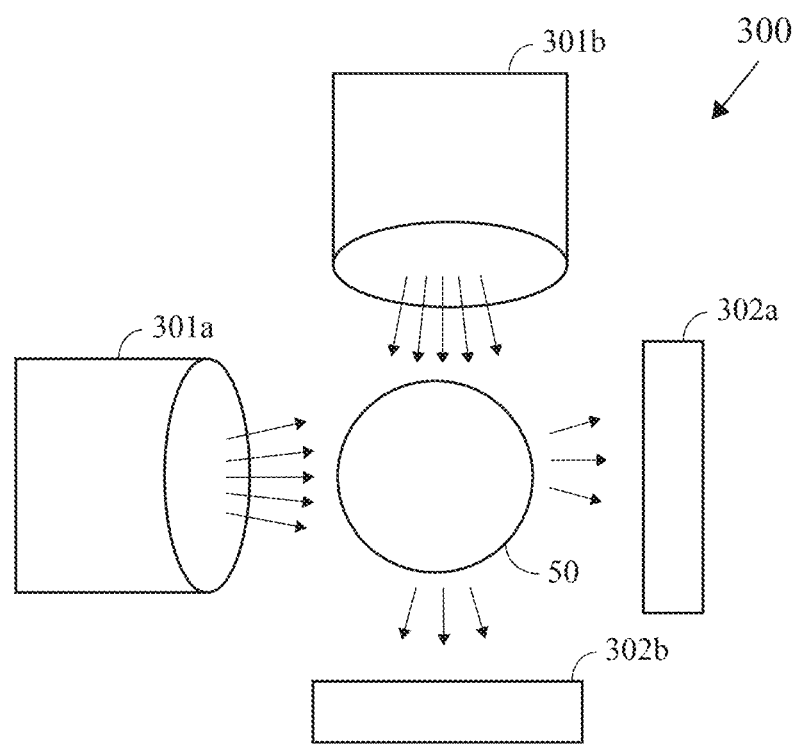
FIG. 3 is an illustration of an X-ray scanning apparatus.

As shown in FIG. 3, an alternative embodiment an X-ray system 300. This embodiment comprises pairs of fixed X-ray sources 301a and 301b, and digital detectors 302a and 302b (analog or digital) that measure perpendicular planes without rotating the golf ball 50. This embodiment eliminates distortion caused when the golf ball 50 rotates. The runout (wobble) of the golf ball can create magnification and parallax issues that impact the precision of the measurement.

Similar to above, the golf ball is presented in front of the two X-ray sources 301a and 301b by using either method below: 1) having the golf ball held by a suction cup attached to a robot; 2) using a robot to place the golf ball on a static fixture.

The detectors 302a and 302b (analog or digital) independently take multiple images. Multiple images (1-24 for analog, 1-8 for digital) are taken by each detector 302a and 302b. An edge detection method is preferably used to determine the diameter or ellipse of the inner and outer edges of the golf ball 50. The X,Z coordinates of the best fit diameter or ellipse of the inner and outer edges are calculated for source one. Y,Z coordinates of the best fit diameter or ellipse of the inner and outer edges are calculated for source two. The Y,Z and X,Z images are combined to calculate 3D distance. The concentricity of the inner and outer edges are preferably calculated using Euclidean distances (3D distance between the center of inner sphere or ellipsoid and outer sphere or ellipsoid).

Samples are evaluated against input criteria and sorted. Based on the criteria, the sample will be moved into the appropriate sorting chute and released. The next sample is picked up and presented in front of the X-ray sources to repeat the process. Multiple layers can be analyzed with a single set of images (1-24 for analog, 1-8 for digital) as long as the adjacent layers have a visual contrast in the image. This can be achieved by creating different layer densities and/or using different filler materials to create the different X-ray imaging contrast.

Figure 4:
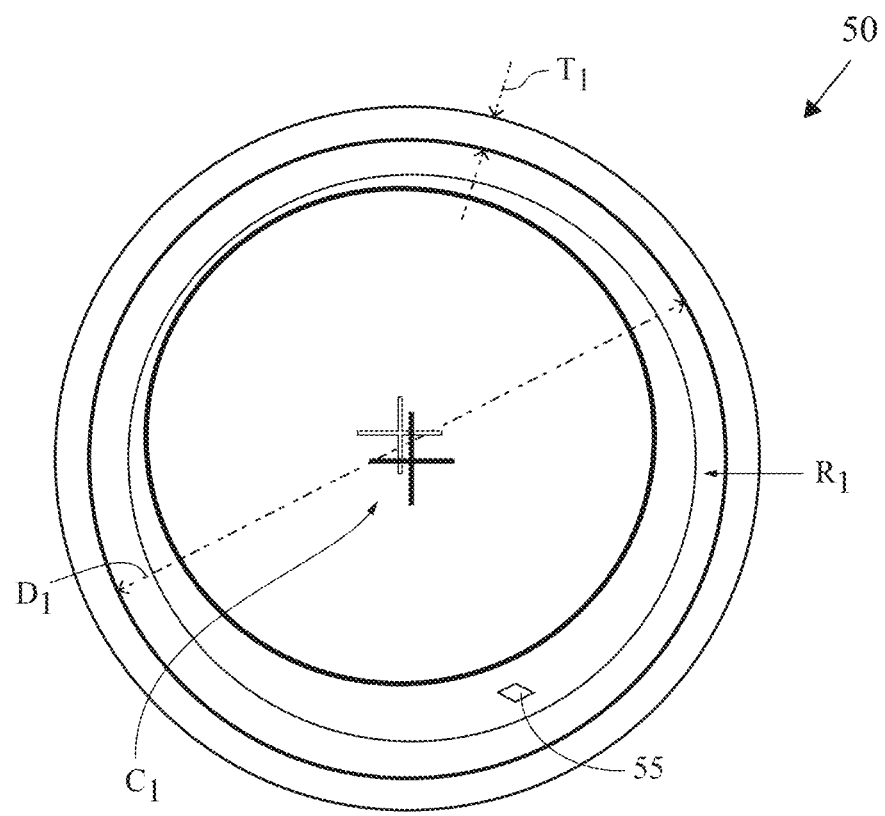
FIG. 4 is an X-ray image of a golf ball.

FIG. 4 is an X-ray image of a golf ball. FIG. 4 illustrates the measurement variables utilized in analyzing an X-ray image of a golf ball 50. One variable is the concentricity (centering of two circles) C1 which involves any inner layer compared to any outer layer. Another variable is the diameter D1 of a core or any outer layer. Another variable is the roundness R1 of a core or any outer layer. The roundness is the value obtained by dividing the difference between the maximum and minimum diameters by two. Another variable is the thickness T1 of any outer layer which is an average of the whole plain or locally in different regions. Another variable is the defects or inclusions 55 in any layer(s).

FIGS. 5A-5F illustrate a best-fit analysis. For a best-fit ellipse analysis, the machine's software identifies preferably at least eighty points around a vicinity of an edge using pixel analysis of the color contrast. The best-fit ellipse is generated using the eighty points for the inner and outer layers. The ellipse is defined by a major and minor diameter and can be averaged for a circular diameter if desired. The centerpoint can also be calculated in the X-Z, Y-Z, or X-Y-Z coordinate plane/space. This method can determine: the concentricity of an inner layer to an outer layer; the diameter of a sample or internal layer (average of minor and major axis values); the roundness of the sample or internal layer; and the thickness of a layer (difference in diameters between best fit ellipses).

Figure 5A:
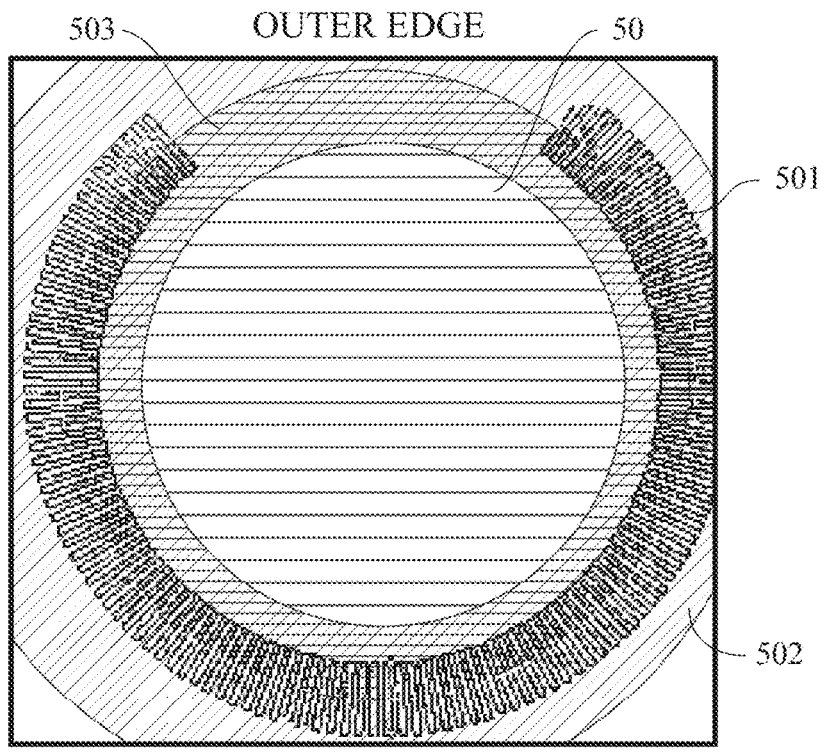
FIG. 5A is an X-ray image of a golf ball illustrating an edge find technique.

FIG. 5A is an X-ray image of a golf ball 50 illustrating an outer edge, edge find technique. An edge find illumination 501 and an edge find component 503 provide a color contrast against a background illumination 502.

Figure 5B:
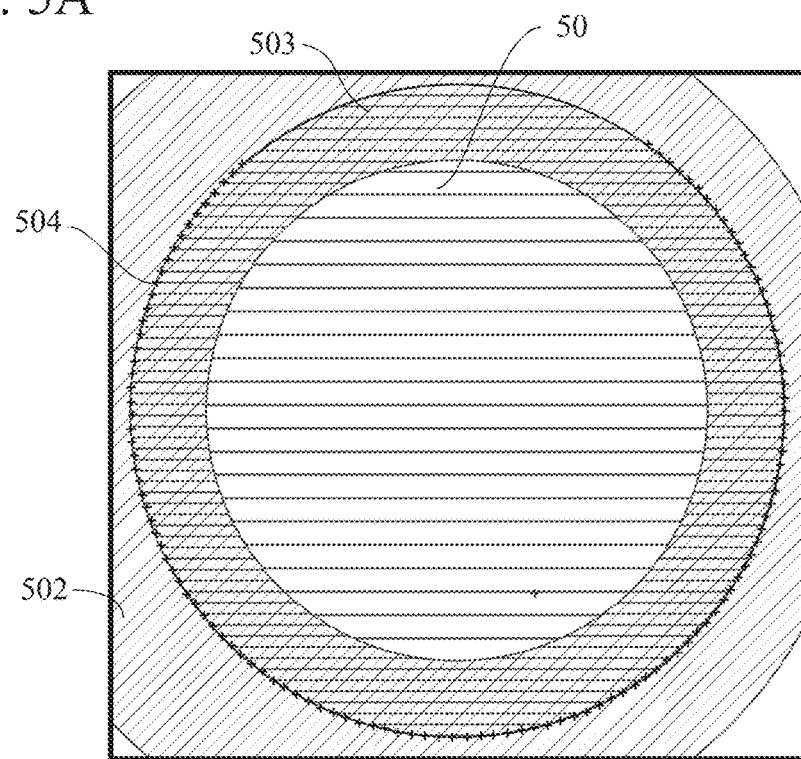
FIG. 5B is an X-ray image of a golf ball illustrating a best fit ellipse.

FIG. 5B is an X-ray image of a golf ball 50 illustrating an outer edge best fit ellipse wherein a best-fit illumination 504 and an edge find component 503 provide a color contrast against a background illumination 502.

Figure 5C:
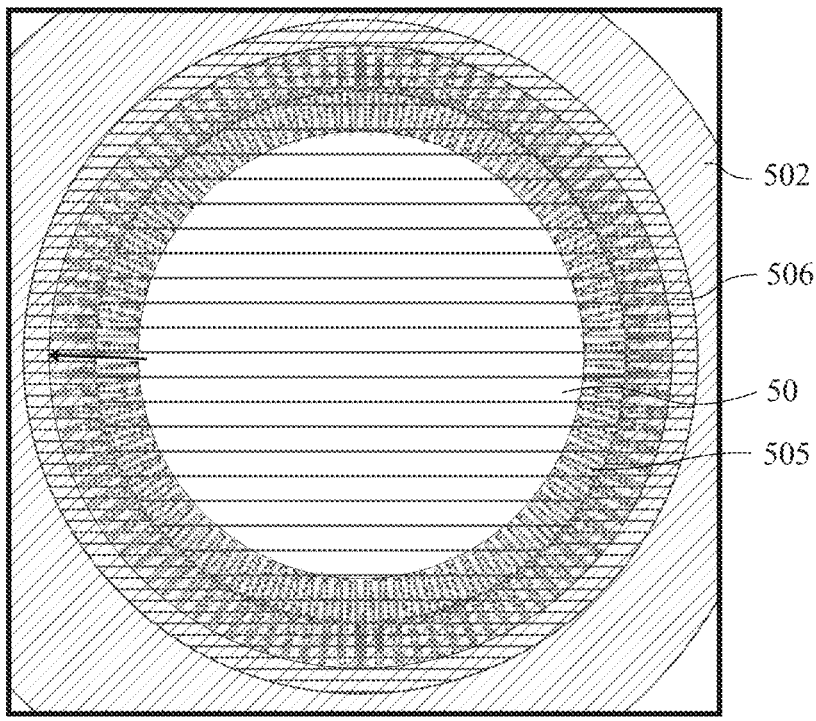
FIG. 5C is an X-ray image of a golf ball.

FIG. 5C is an X-ray image of a golf ball 50 illustrating an inner edge, edge find technique. An edge find illumination 505 and an edge find component 506 provide a color contrast against a background illumination 502.

Figure 5D:
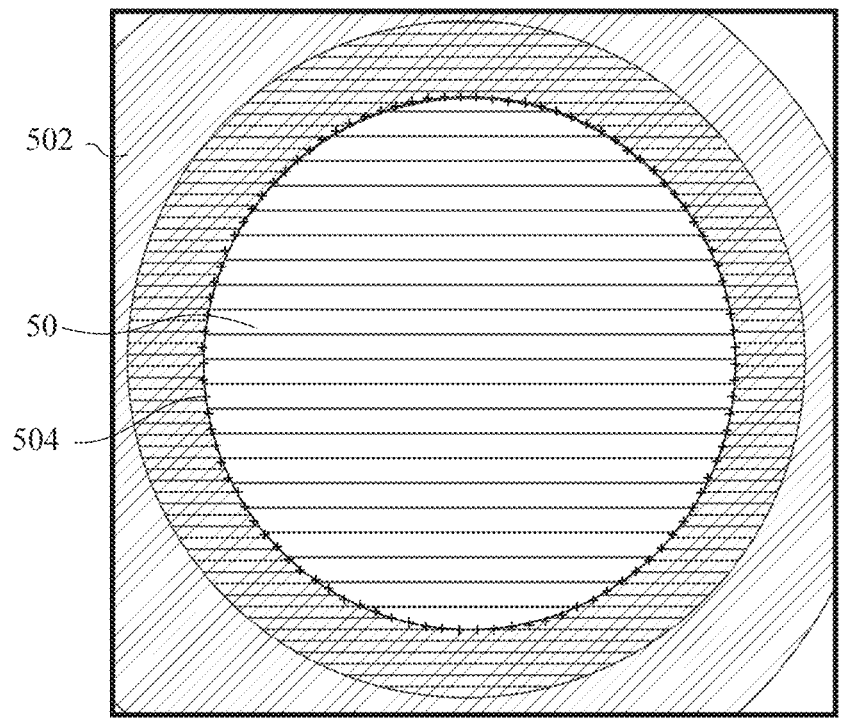
FIG. 5D is an X-ray image of a golf ball.

FIG. 5D is an X-ray image of a golf ball 50 illustrating an inner edge best fit ellipse wherein a best-fit illumination 504 provide a color contrast against a background illumination 502.

Figure 5E:
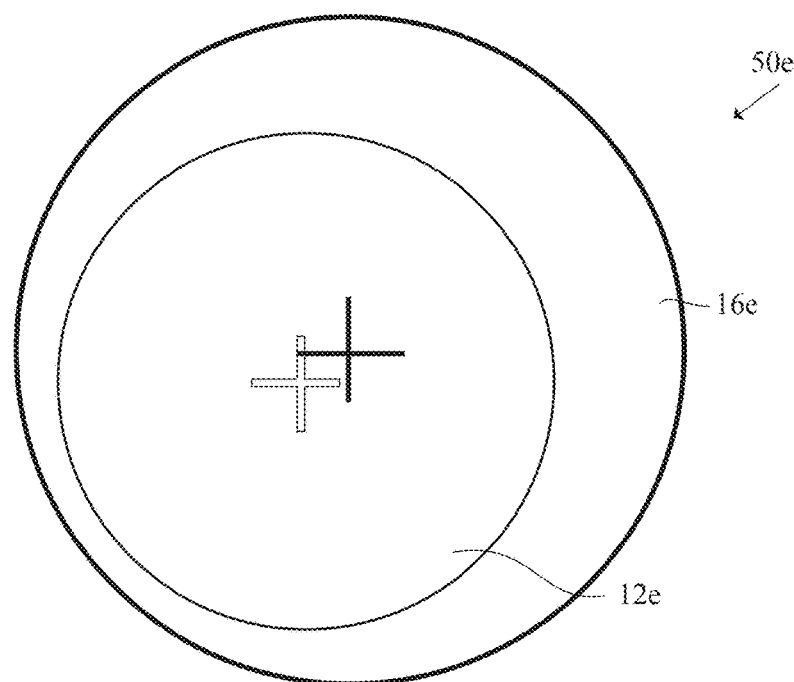
FIG. 5E is an X-ray image of a golf ball.

FIG. 5E is an off-center example of an X-ray image of a golf ball 50e showing the core 12e and the cover 16e.

Figure 5F:
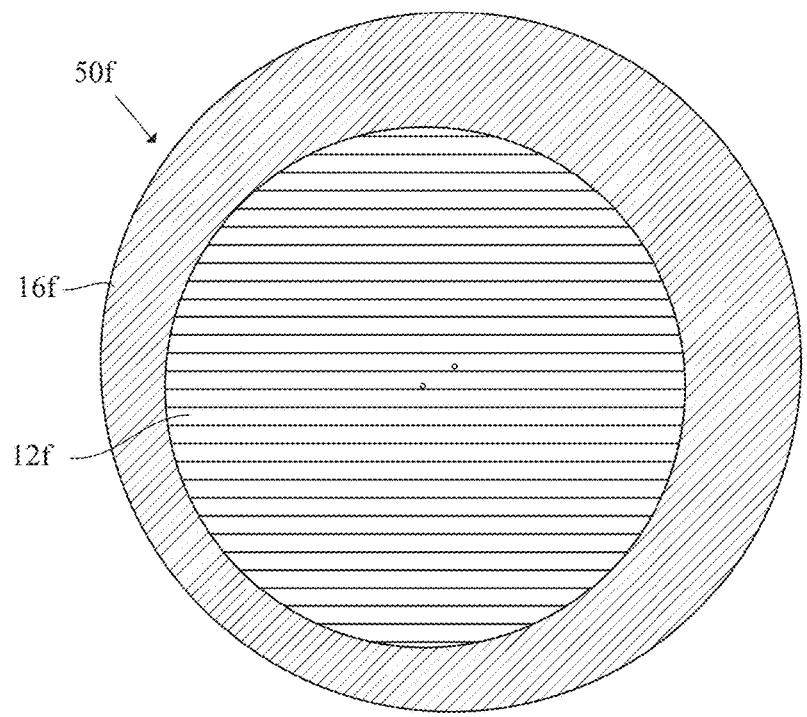
FIG. 5F is an X-ray image of a golf ball.

FIG. 5F is an off-center example of an X-ray image of a golf ball 50f showing the core 12f and the cover 16f.

Figure 6A:
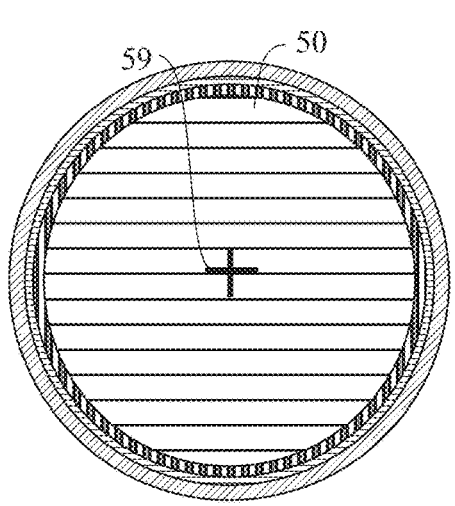
FIG. 6A is a pixel image of a golf ball.
Figure 6B:
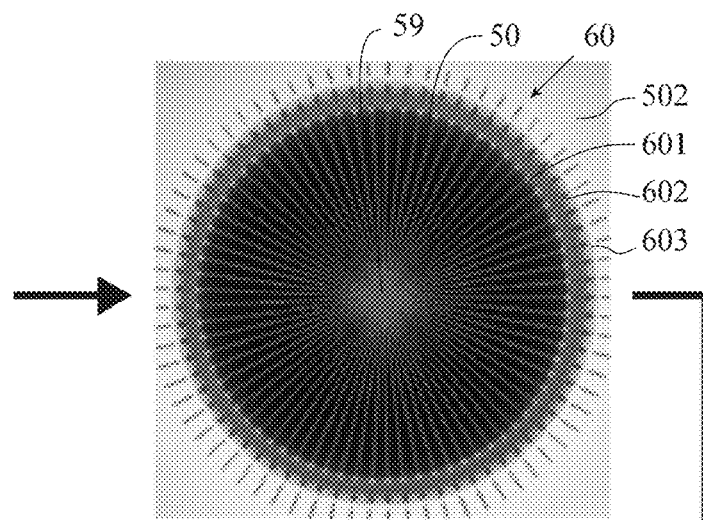
FIG. 6B is a pixel image of a golf ball.
Figure 6C:
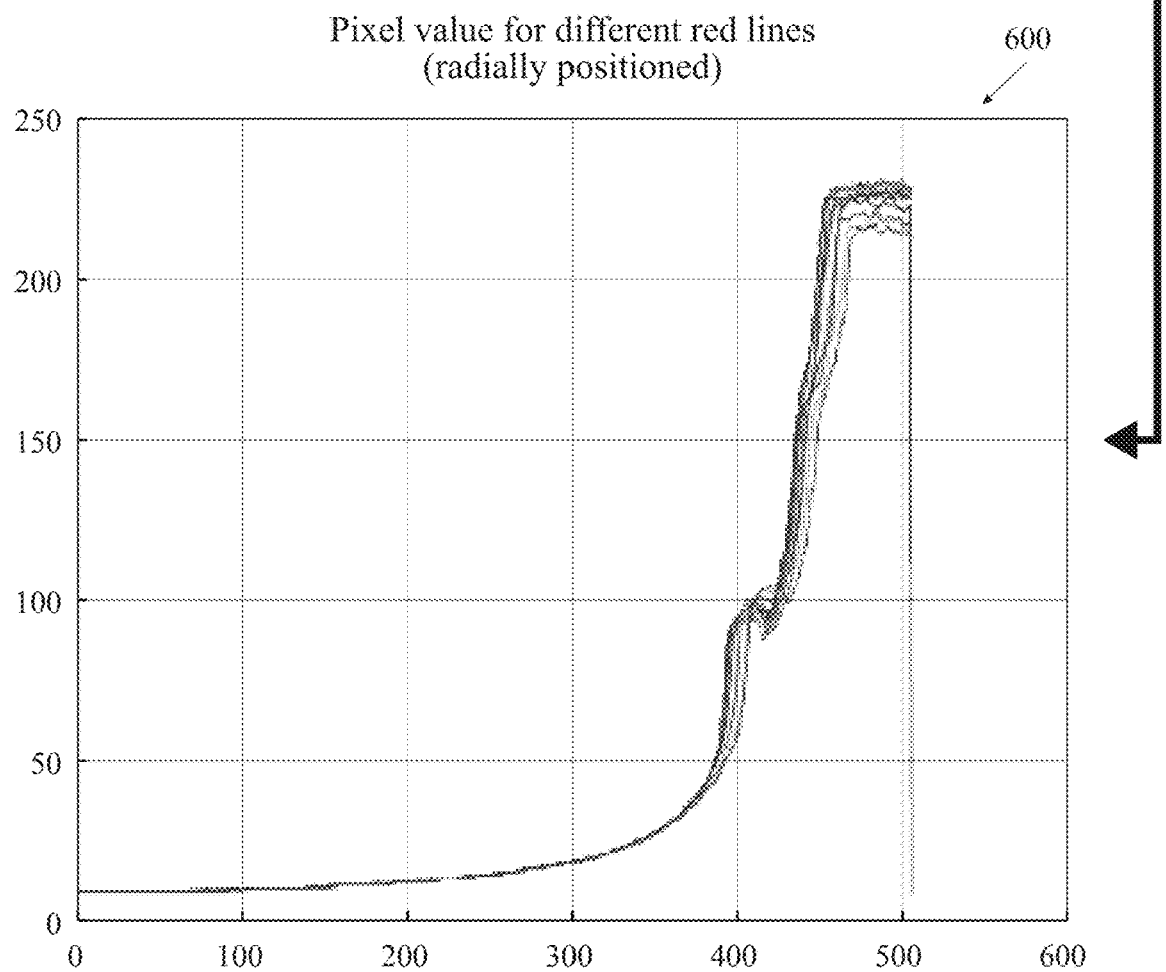
FIG. 6C is a graph of pixel values.

FIG. 6A is a pixel image of a golf ball 50 with a center 59. FIG. 6B is a pixel image of a golf ball 50 with radial rays from the center 59. After the image is obtained as shown FIG. 6A, Matlab is utilized to identify different layers of the ball. As shown in FIG. 6B, radial rays 60 are created from the center 59 of the golf ball 50 outwards and the pixel value along the radial ray 60 is plotted and analyzed. Layers are shown by pixel circles 601, 602 and 603. The fidelity (or spacing) of the radial rays 60 can be adjusted and optimized for resolution and analysis speed. FIG. 6C is a graph 600 of pixel values for different lines from FIG. 6B. There is a "plateau" at about y=100 (x=400) and at y=220 (x=450) that would indicate an edge.

Figure 7A:
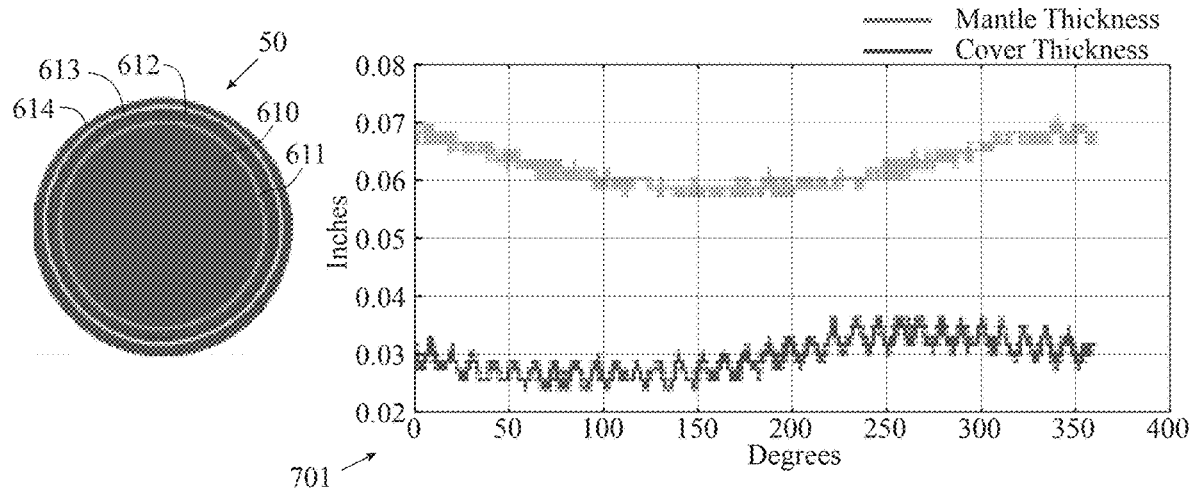
FIG. 7A is a graph of pixel values.
Figure 7B:
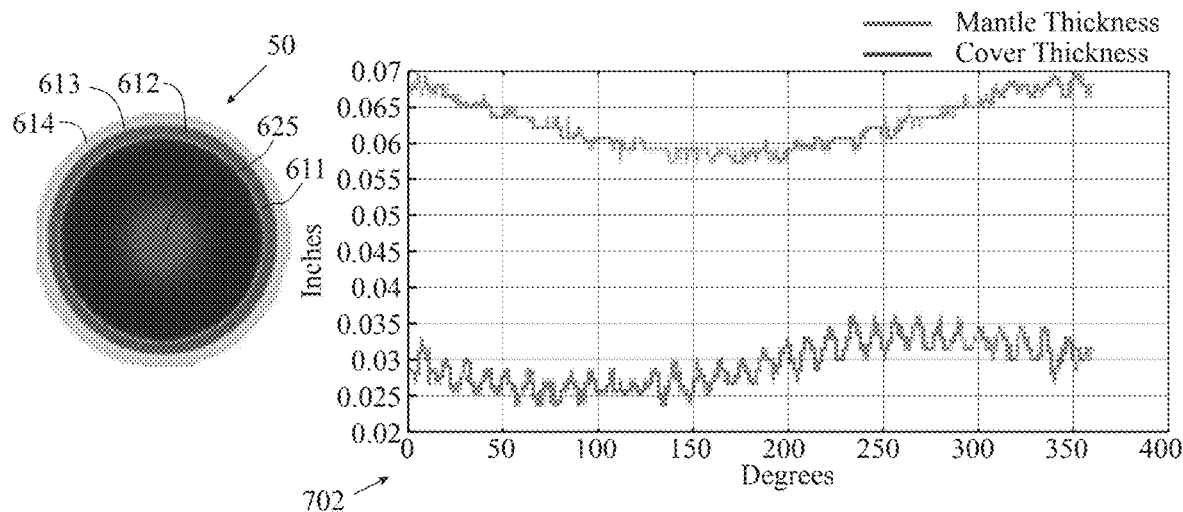
FIG. 7B is a graph of pixel values.
Figure 7C:
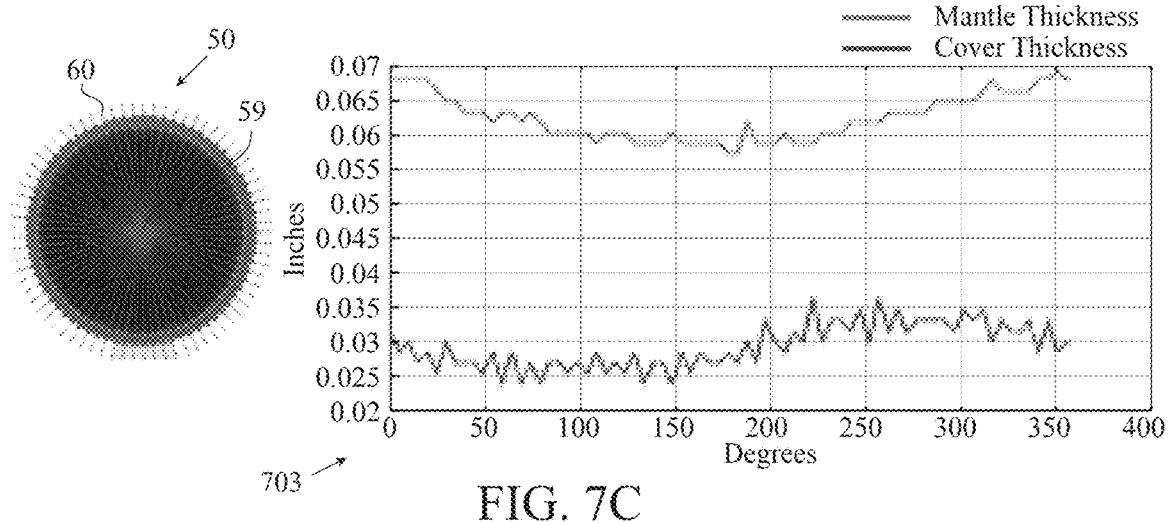
FIG. 7C is a graph of pixel values.

FIG. 7A is a graph of pixel values from the golf ball image 50 with layers 610-614 at 0.1 degrees radial line spacing. FIG. 7B is a graph of pixel values from the golf ball image 50 with layers 611-614, and center 625 at 1 degree radial line spacing. FIG. 7C is a graph of pixel values from the golf ball image 50 with a center 59 and radial rays 60, at 5 degrees radial line spacing. The pixel values along the radial ray are analyzed and finding changes in the pixel values enables edge detection of layers. This method is applied to multiple layers along the same radial ray if each layer shows different contrast. Analysis also indicates if a core/insert layer thickness is uneven based on the magnitude of the sinusoidal pattern. The sinusoidal pattern shows that this ball is off-center for the core to mantle and the mantle to the cover. A horizontal line would show a layer of constant thickness.

Figure 8:
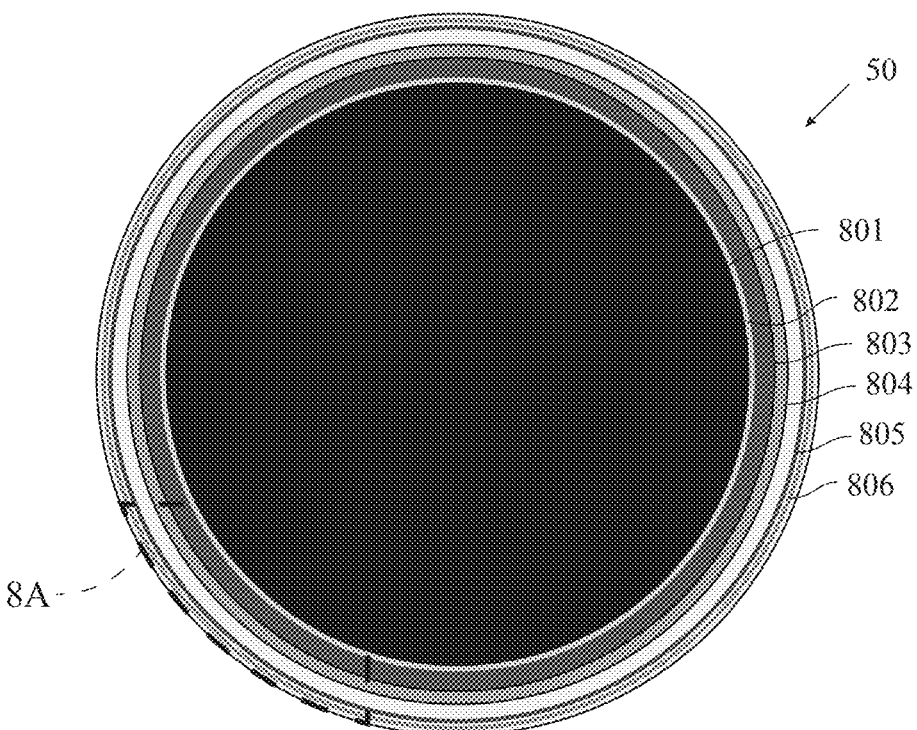
FIG. 8 is an X-ray of a golf ball.
Figure 8A:
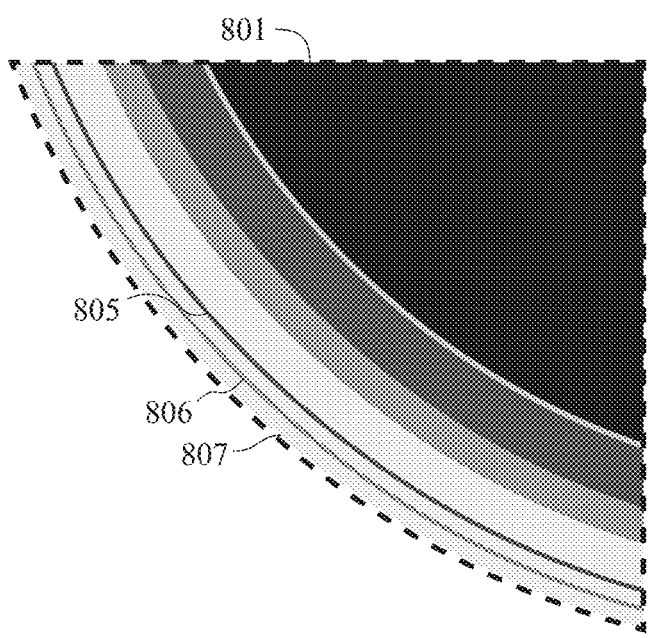
FIG. 8A is an isolated view of a portion of an X-ray of a golf ball.

FIG. 8 is an X-ray of a golf ball 50. FIG. 8A is an isolated view of a portion of an X-ray of a golf ball 50. FIGS. 8 and 8A, illustrate images for analysis to identify a cover outer region. Due to the surface geometries on the cover of a golf ball 50, the cover thickness needs a unique methodology. Starting with a circle 806 that has a diameter such that it is outside of the cover and decreasing the diameter in small increments 805-801 (or starting with the diameter of the outer mantle and increasing the diameter in small increments) the edge can be found by: calculating the average pixel value for the complete to be a certain threshold, and finding four or more prominent peaks.

Figure 9:
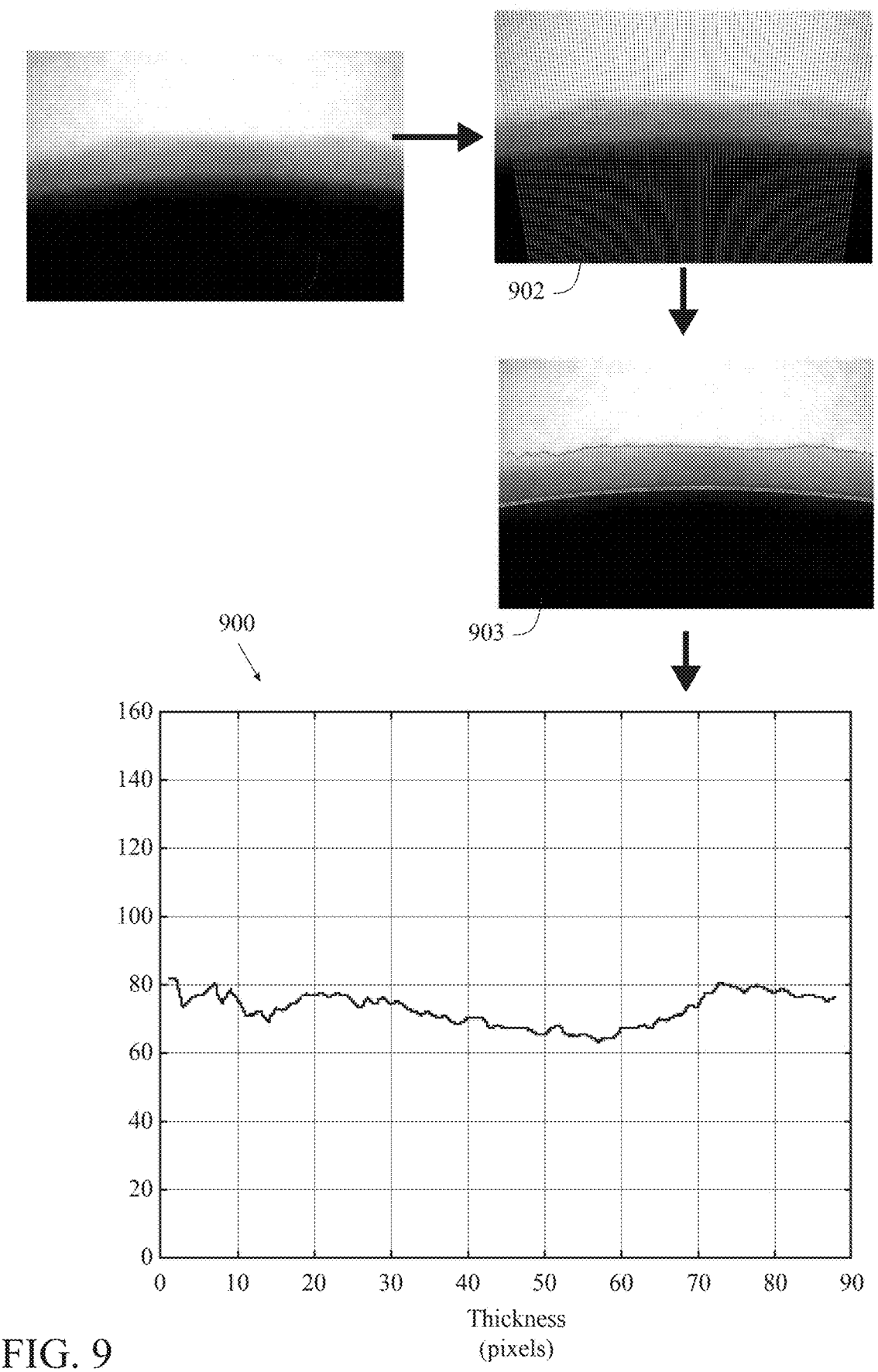
FIG. 9 is a graph of thickness based on pixels.

FIG. 9 shows a process for producing a graph of thickness based on pixels. An initial image 901 is generated. Then at 902 an image with multiple radial rays from a center through the cover is generated. In the image at 903, for each line, edge detection techniques are used to locate the edges of the outer mantle (blue line) and cover (green line). In this case, moving averages were used. With the known edges, the outer edge (cover) is subtracted from the inner edge (outer mantle) to produce a cover thickness in pixels. This is converted to inches or mm with a simple calibration to produce the graph 900.

Figure 10:
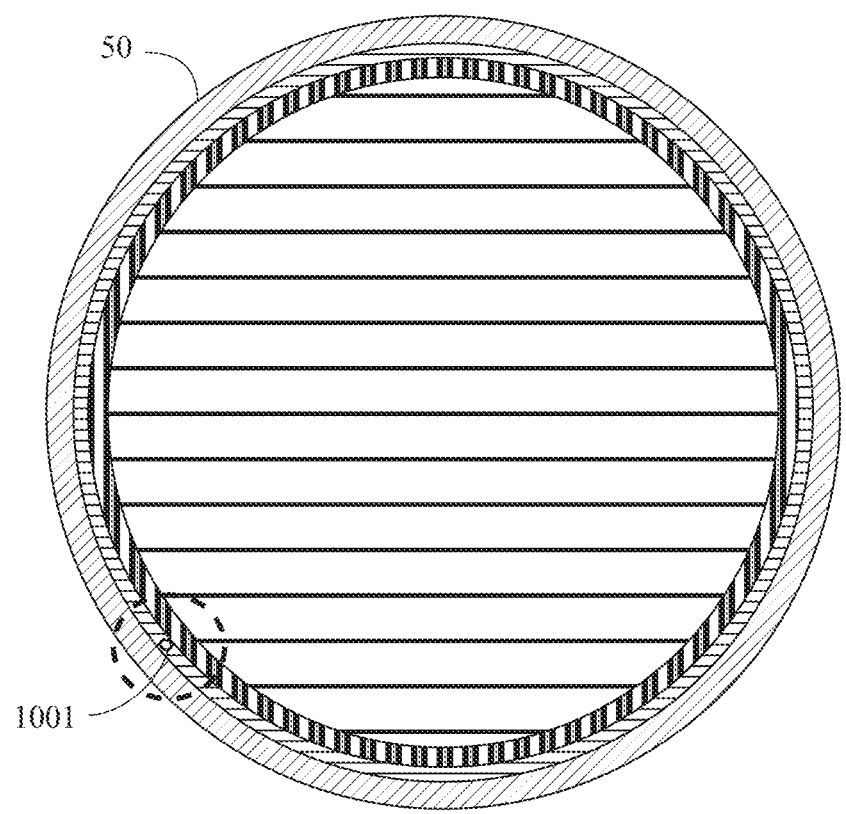
FIG. 10 is an X-ray image of a golf ball.

FIG. 10 is an X-ray image of a golf ball 50. Using the image taken by the X-ray unit, an operator can interrogate a layer for an inclusion 1001. The inclusion 1001 appears as a difference pixelated color indicating it has a significantly different density. When this occurs in the rubber recipe, it is normally darker and indicates that powders are not adequately dispersed within the polymer matrix. An inclusion could lead to a premature durability failure. When an inclusion is found, the software can compare it against a set of criteria and sort the defective sample accordingly.

Figure 11:
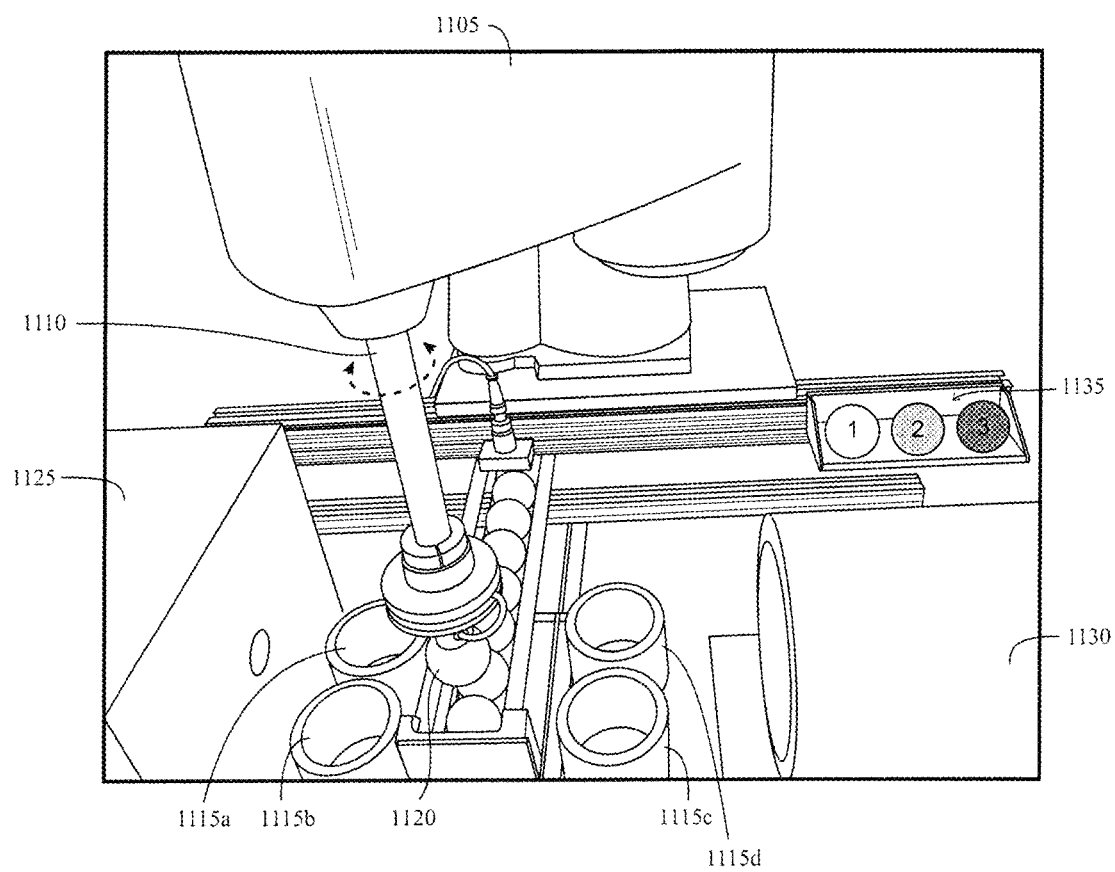
FIG. 11 is a top perspective view of an X-ray scanning apparatus.

FIG. 11 is a top perspective view of an X-ray scanning apparatus. A pick and place robot 1105 is preferably used for sorting the imaged golf balls using an arm 1110 that has vertical and rotational movement. An X-ray source 1125 working in conjunction with a digital detector 1130 generates X-ray images (preferably at 0 and 90 degrees) of the golf ball 1120, which are analyzed and used to sort the golf ball 1120 into conduits 1115a-1115d. Calibration standards 1135 include a golf ball, a core and a dual core. X-ray images are collected on two or more axis on various layers of a golf ball at various stages of construction-core (dual or single), mantle(s) on a core, or covered mantle or covered core-to determine layer diameters, layer concentricities in 3D and identify inclusions. Preferred sorting machines sort samples based on diameters and concentricity. Alternatively, sorting machines also use inclusion identification sorting, with artificial intelligence (AI) used to detect inclusions.

Figure 12:
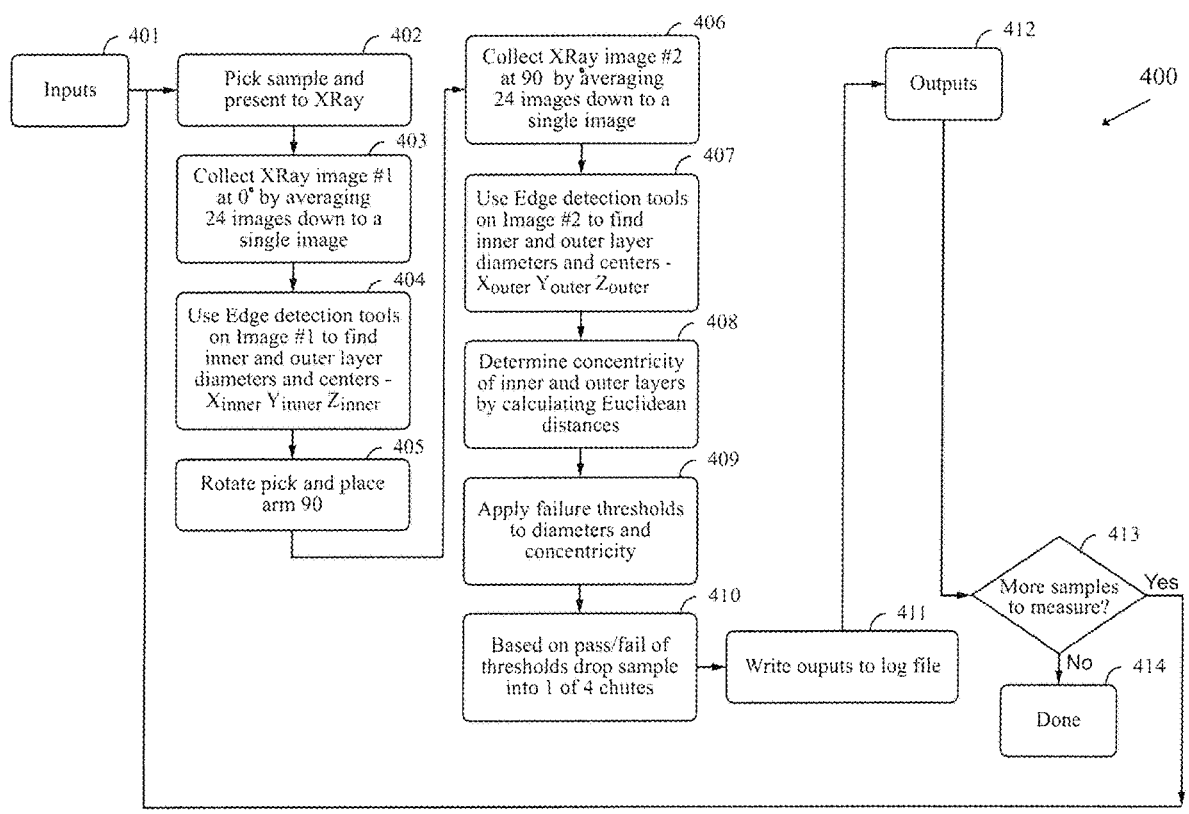
FIG. 12 is a flow chart diagram of a method for scanning golf balls with an X-ray scanning apparatus.

FIG. 12 is a flow chart diagram of a method 400 for scanning golf balls with an X-ray scanning apparatus following steps 410-414.

Figure 13:
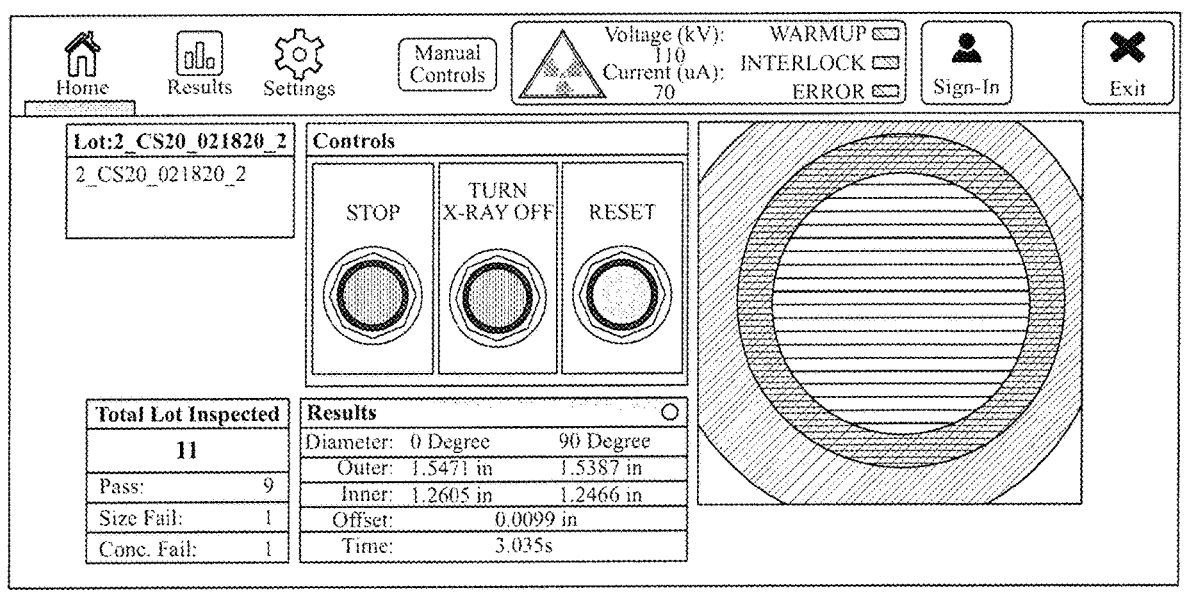
FIG. 13 is an illustration of a user interface for an X-ray scanning apparatus.

FIG. 13 is an illustration of a user interface for an X-ray scanning apparatus. A main screen provides information about machine status, start/stop machine, X-ray power settings, samples type measured, metrics/results, and X-ray image of a current golf ball.

Figure 14:
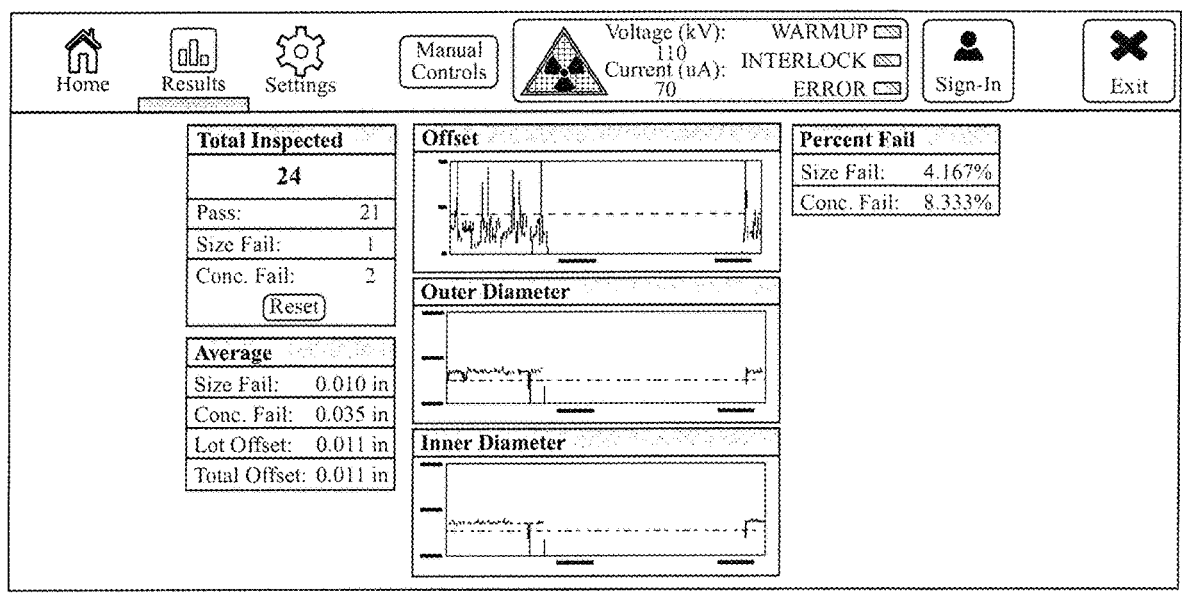
FIG. 14 is an illustration of a user interface for an X-ray scanning apparatus.

FIG. 14 is an illustration of a user interface for an X-ray scanning apparatus. The HMI screen of FIG. 14 is viewed while golf ball measurements are in progress.

Figure 15:
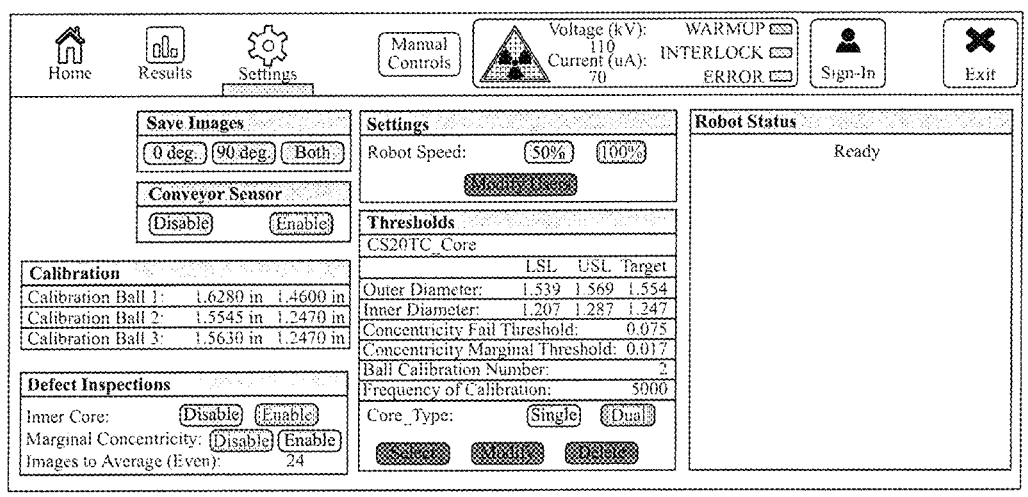
FIG. 15 is an illustration of a user interface for an X-ray scanning apparatus.

FIG. 15 is an illustration of a user interface for an X-ray scanning apparatus. The screen is FIG. 15 is where an operator enters additional inputs to the process. The operator enters additional inputs to the process. At the save images tab, the machine is asking if the X-ray images generated during measurement should be saved to a network. If so, preferably jpg files are saved. The conveyor sensor is enabled when using a hopper/conveyor feed of samples to machine. The calibration tab shows up to three calibration standards that are present inside the main measurement area of the X-ray cabinet. These are basically 'golden parts', i.e. dual core, dual core with a single mantle, single core with a dual mantle. The standards preferably have a concentricity tolerance of ±0.0005 inch. The defect inspection functions are as follows: The inner core function is enabled if an operator wants the machine to measure and sort by inner core diameter. The disable marginal concentricity function is enabled if the operator wants the machine to sort using two levels of concentricity. For example, a top level product for tour players has a tighter tolerance than regular production tolerances. If enabled, the machine will sort samples into two separate fiber drums 'tour certified' and 'production' based on thresholds listed in the thresholds section. The images to average (Even) function is the number of images taken by the sensor and averaged down to one image at both 0° and 90°. The settings function sets a speed of the SCARA robot.

Figure 16:
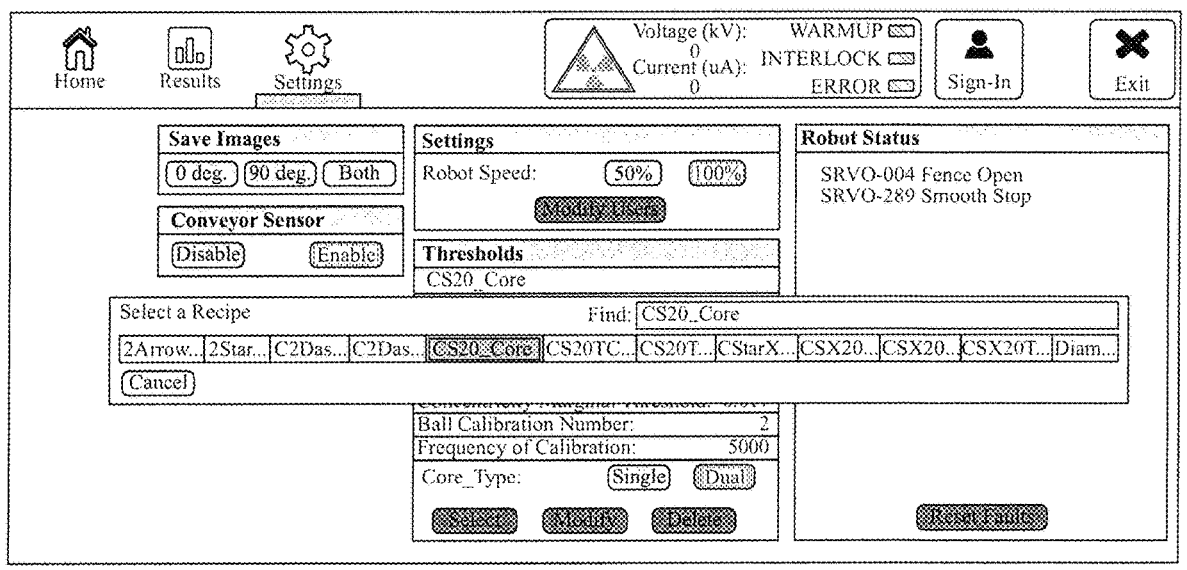
FIG. 16 is an illustration of a user interface for an X-ray scanning apparatus.

FIG. 16 is an illustration of a user interface for an X-ray scanning apparatus. The HMI screen showing the thresholds function. The thresholds include: an outer diameter with a nominal target along with USL and LSL in inches; an inner diameter with a nominal target along with USL and LSL in inches; a concentricity fail threshold; a concentricity marginal threshold; and a ball calibration number.

Figure 17:
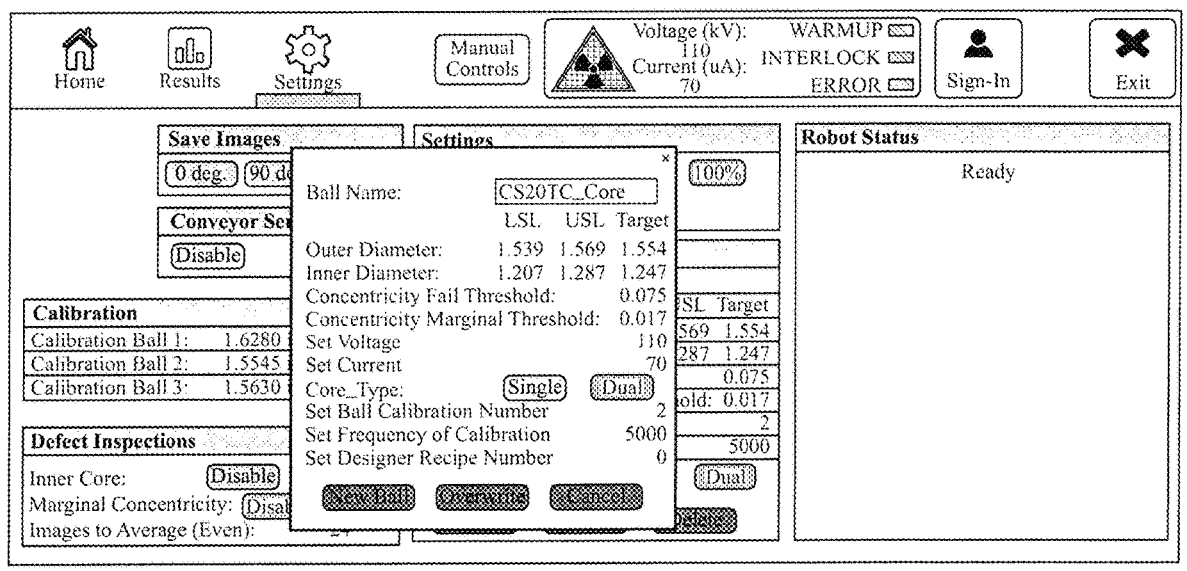
FIG. 17 is an illustration of a user interface for an X-ray scanning apparatus.

FIG. 17 is an illustration of a user interface for an X-ray scanning apparatus wherein the operator has clicked the select button from the thresholds section.

Figure 18:
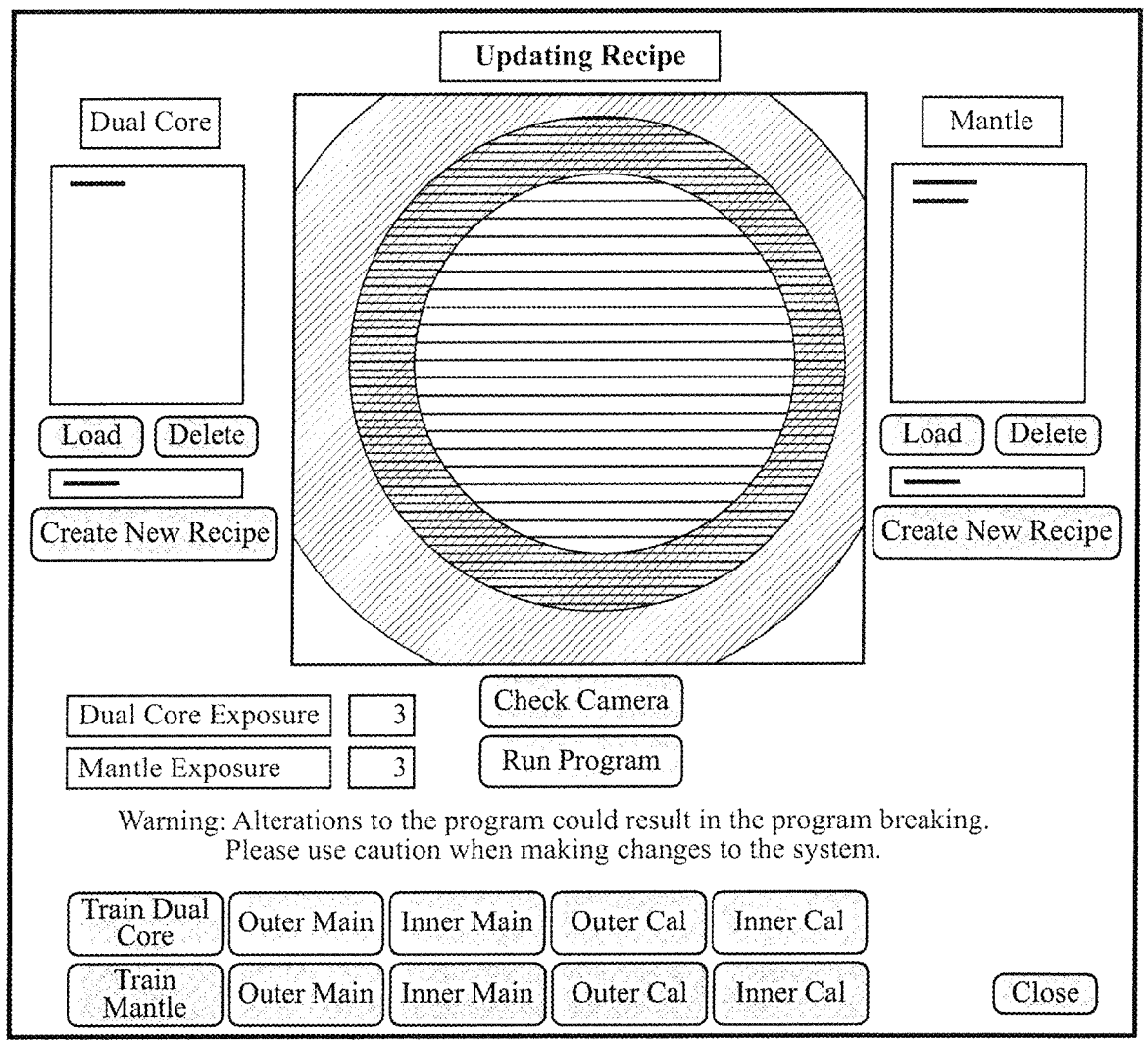
FIG. 18 is an illustration of a user interface for an X-ray scanning apparatus.

FIG. 18 is an illustration of a user interface for an X-ray scanning apparatus.

Figure 19:
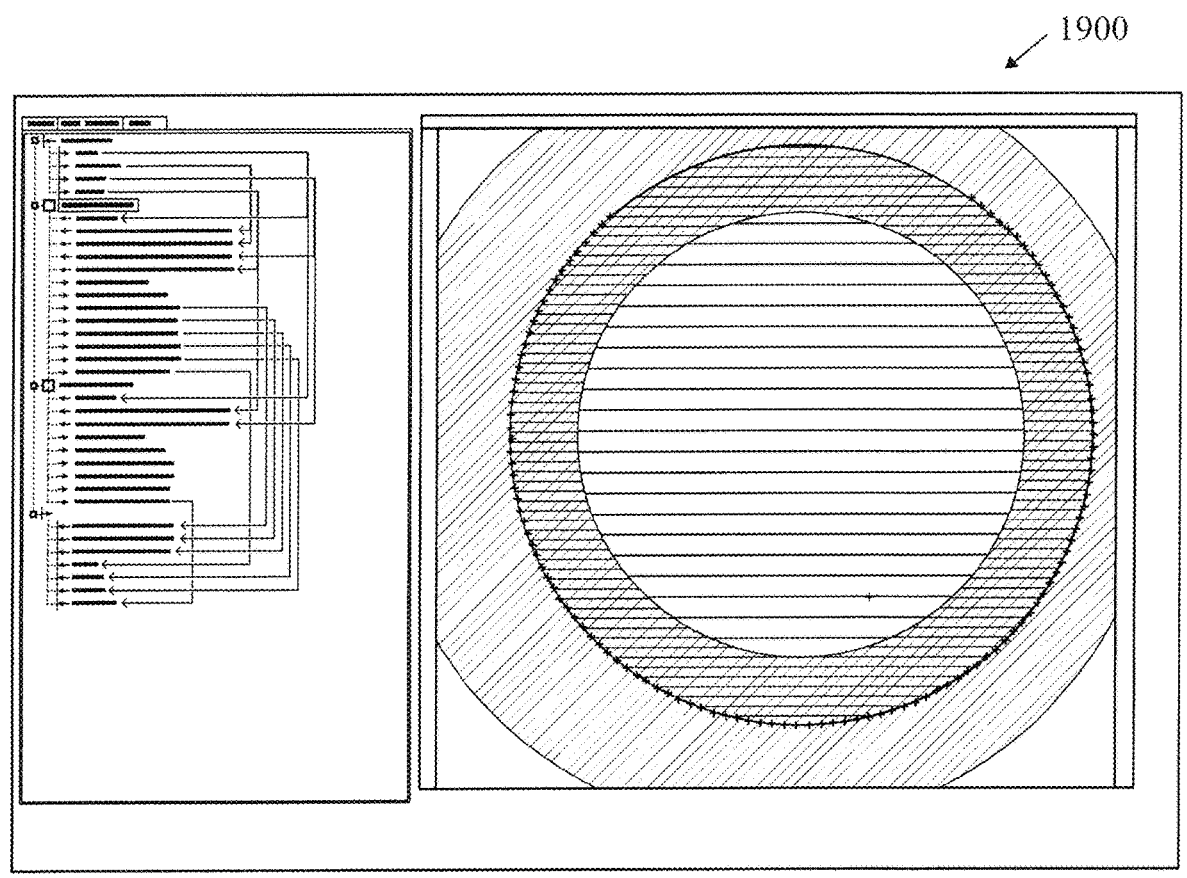
FIG. 19 is an illustration of a user interface for an X-ray scanning apparatus.

FIG. 19 is an illustration of a user interface for an X-ray scanning apparatus with an image 1900 for edge detection.

Figure 20:
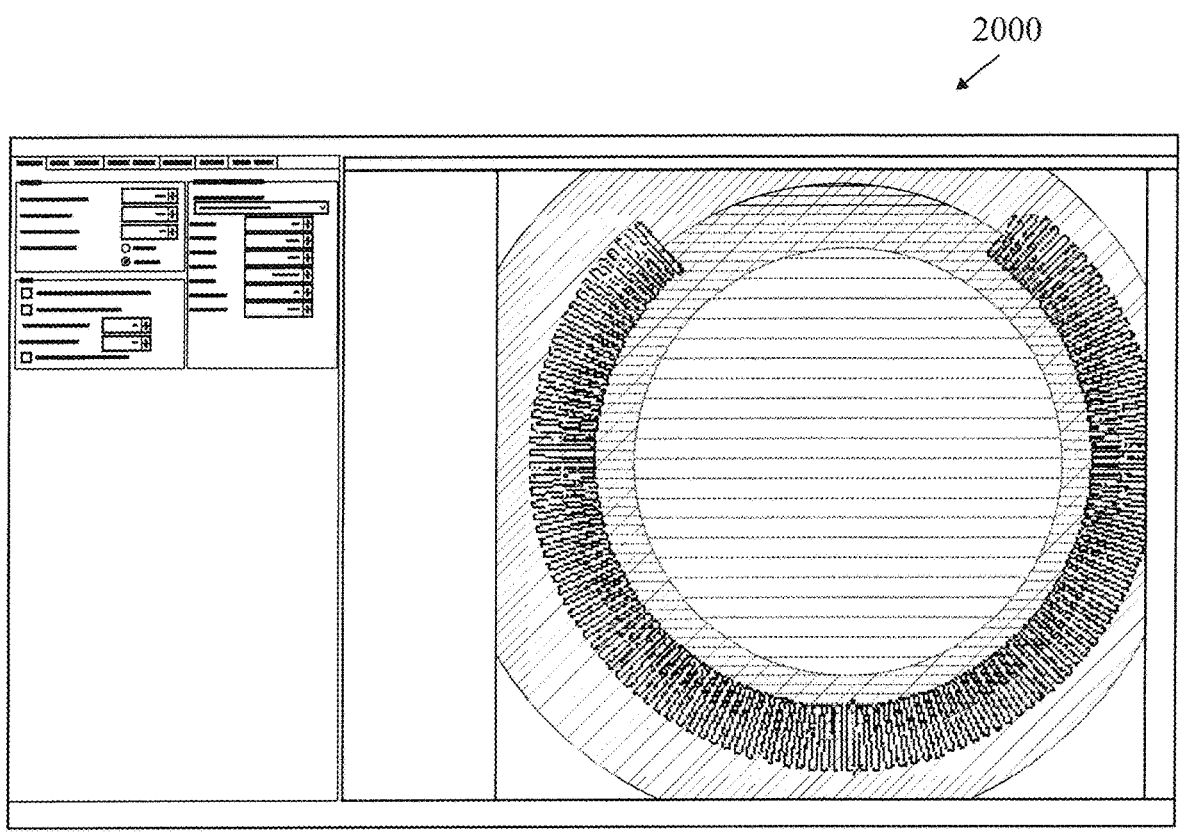
FIG. 20 is an illustration of a user interface for an X-ray scanning apparatus.

FIG. 20 is an illustration of a user interface for an X-ray scanning apparatus with an image 2000 for edge detection.

Figure 21:
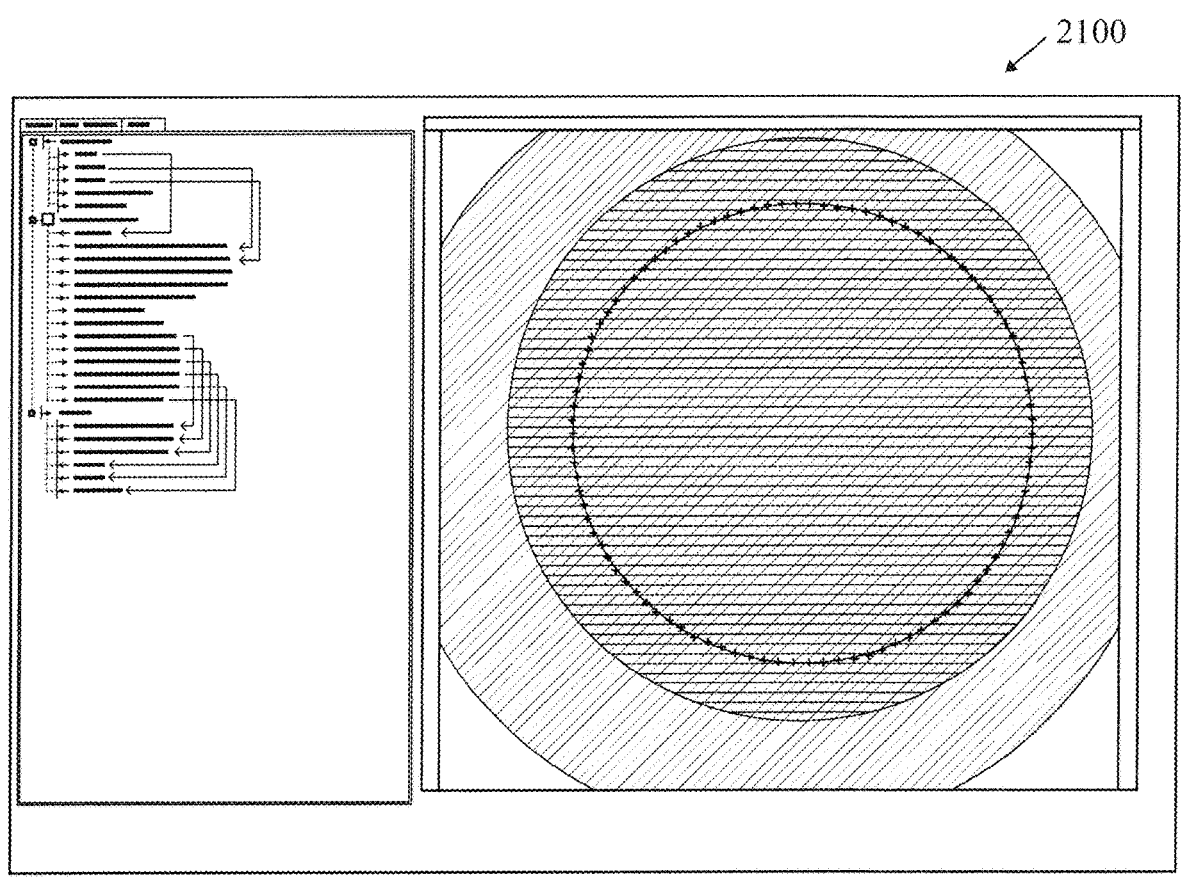
FIG. 21 is an illustration of a user interface for an X-ray scanning apparatus.

FIG. 21 is an illustration of a user interface for an X-ray scanning apparatus with an image 2100 for inner layer edge detection.

Figure 22:
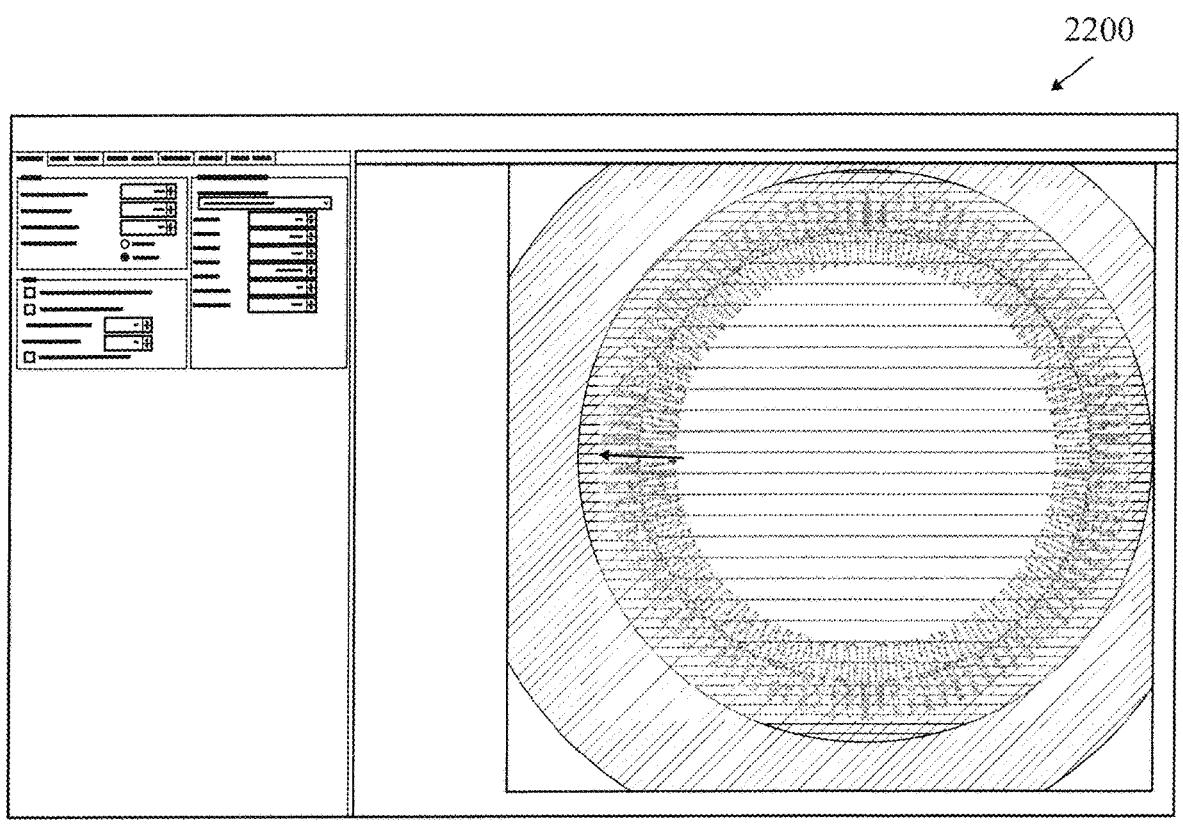
FIG. 22 is an illustration of a user interface for an X-ray scanning apparatus.

FIG. 22 is an illustration of a user interface for an X-ray scanning apparatus with an image 2200 for inner layer edge detection.

Figure 23:
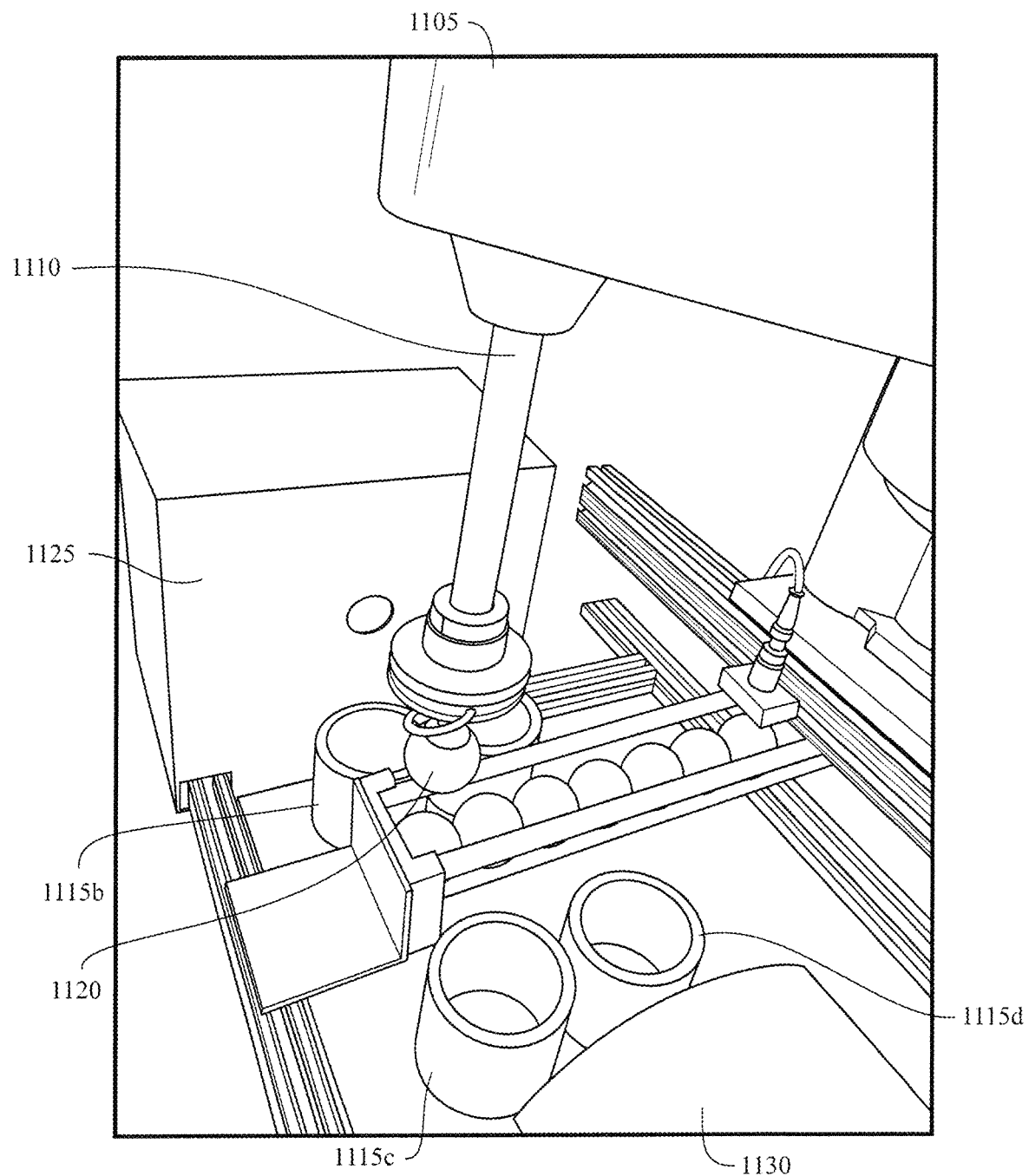
FIG. 23 is a top perspective view of an X-ray scanning apparatus.

FIG. 23 is a top perspective view of an X-ray scanning apparatus. A pick and place robot 1105 is preferably used for sorting the imaged golf balls using an arm 1110 that has vertical and rotational movement. An X-ray source 1125 working in conjunction with a digital detector 1130 generates X-ray images (preferably at 0 and 90 degrees) of the golf ball 1120, which are analyzed and used to sort the golf ball 1120 into conduits 1115*b*-1115*d*.

Figure 24:
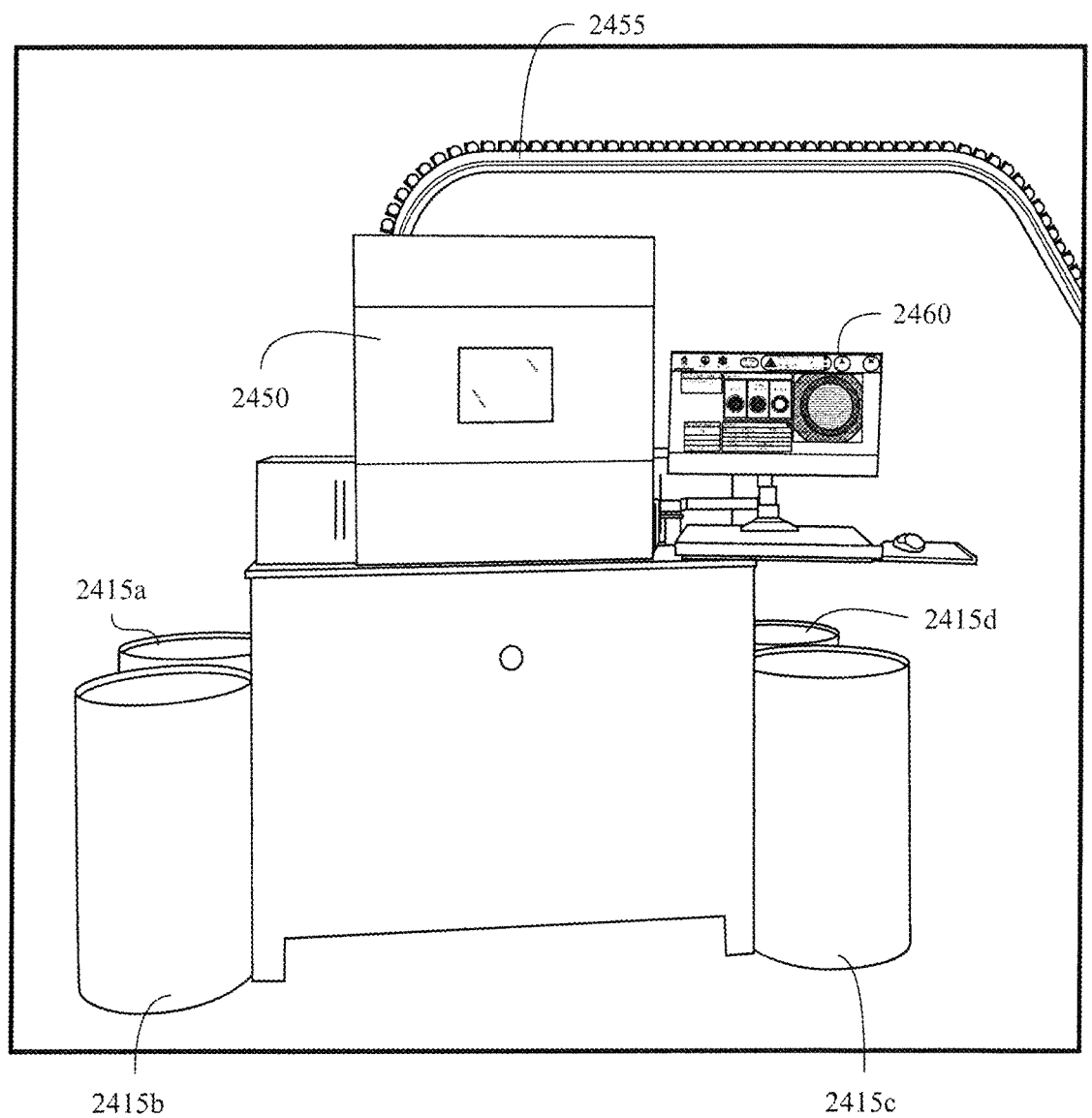
FIG. 24 is a front elevation view of an X-ray scanning apparatus.

FIG. 24 is a front elevation view of an X-ray scanning apparatus 2450 which preferably includes a conveyor 2455, and a user interface 2460. Sorting bins 2415*a-d* are also shown.

Figure 25:
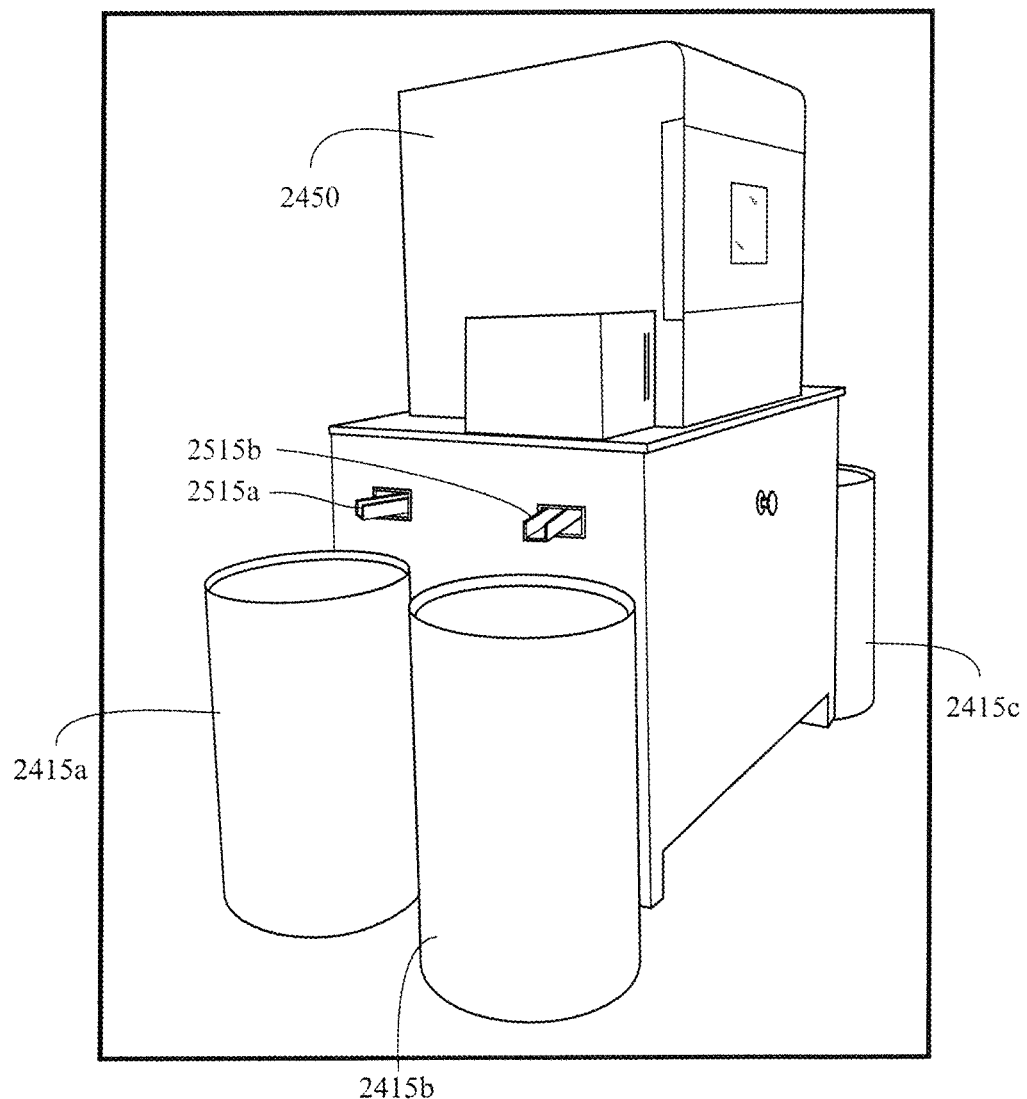
FIG. 25 is a front perspective view of an X-ray scanning apparatus.

FIG. 25 is a front perspective view of an X-ray scanning apparatus 2450 which includes conduits 2515*a-b* for golf balls to be sorted into bins 2415*a-b*.

Figure 26:
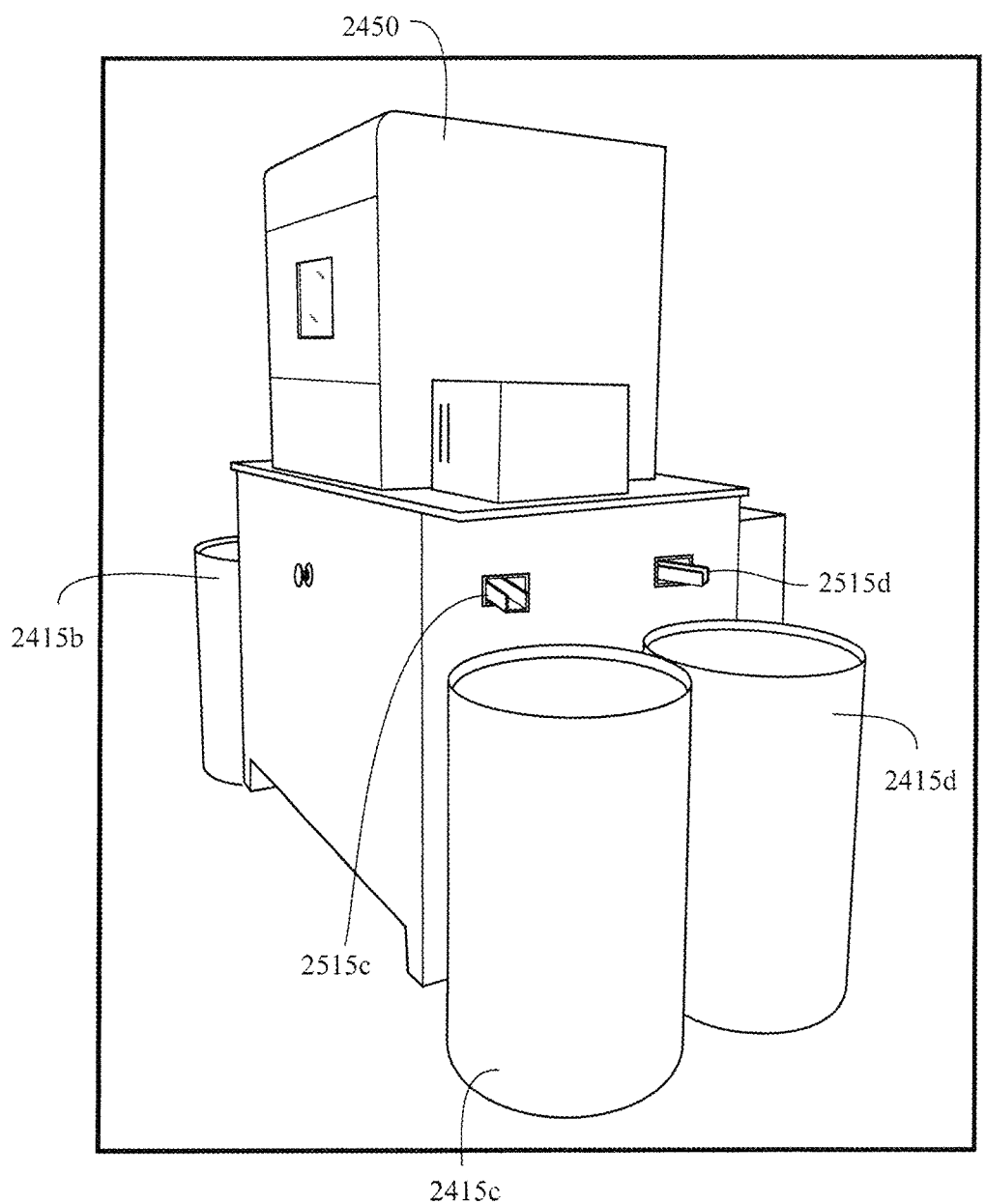
FIG. 26 is a rear perspective view of an X-ray scanning apparatus.

FIG. 26 is a rear perspective view of an X-ray scanning apparatus 2450 which includes conduits 2515*c-d* for golf balls to be sorted into bins 2415*c-d*.

Figure 27:
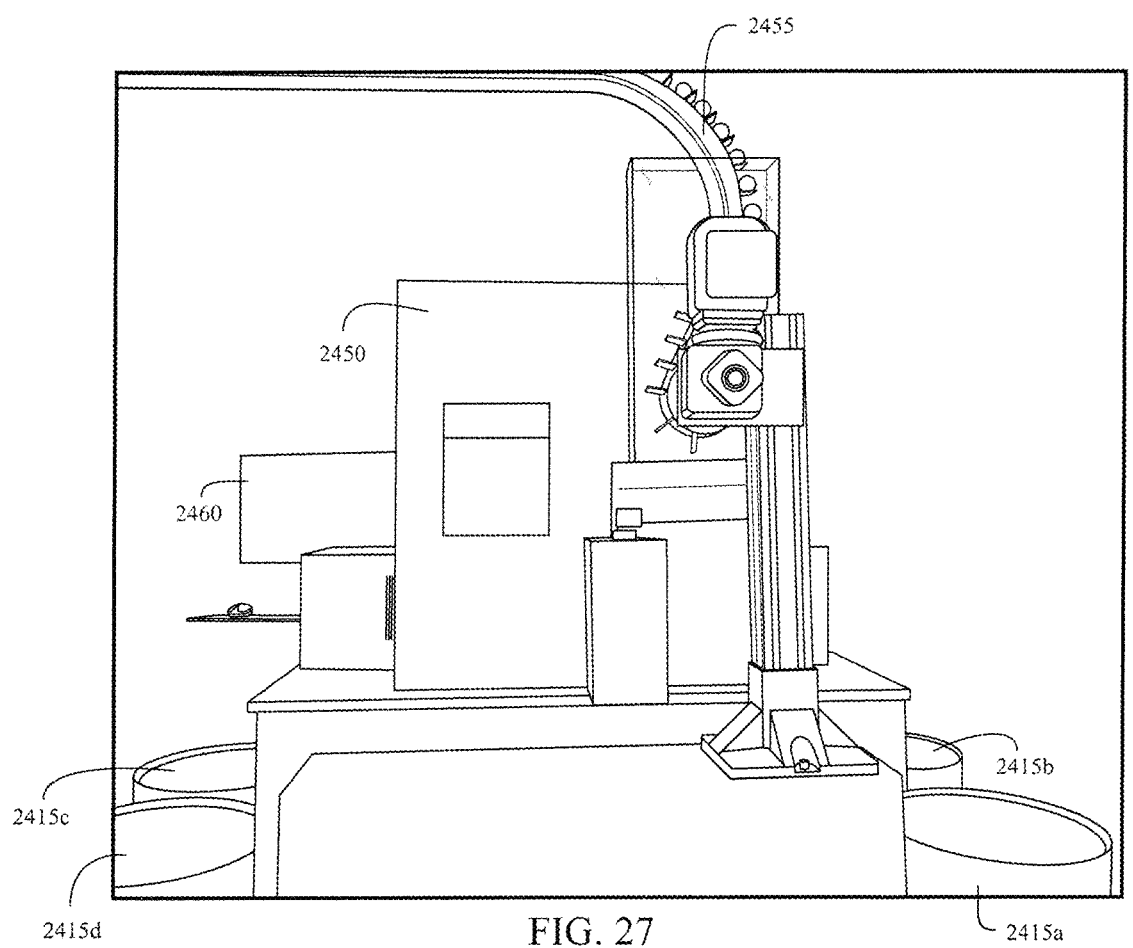
FIG. 27 is a side elevation view of an X-ray scanning apparatus.

FIG. 27 is a side elevation view of an X-ray scanning apparatus 2450 which preferably includes a conveyor 2455, and a user interface 2460. Sorting bins 2415*a-d* are also shown.

Preferably, the outer core is composed of a polybutadiene material, zinc penta chloride, organic peroxide, zinc stearate, zinc diacrylate and zinc oxide.

In a preferred embodiment, the cover is preferably composed of a thermoplastic polyurethane material, and preferably has a thickness ranging from 0.025 inch to 0.04 inch, and more preferably ranging from 0.03 inch to 0.04 inch. The material of the cover preferably has a Shore D plaque hardness ranging from 30 to 60, and more preferably from 40 to 50. The Shore D hardness measured on the cover is preferably less than 56 Shore D. Preferably the cover 16 has a Shore A hardness of less than 96. Alternatively, the cover 16 is composed of a thermoplastic polyurethane/polyurea material. One example is disclosed in U.S. Pat. No. 7,367,903 for a Golf Ball, which is hereby incorporated by reference in its entirety. Another example is Melanson, U.S. Pat. No. 7,641,841, which is hereby incorporated by reference in its entirety. Another example is Melanson et al, U.S. Pat. No. 7,842,211, which is hereby incorporated by reference in its entirety. Another example is Matroni et al., U.S. Pat. No. 7,867,111, which is hereby incorporated by reference in its entirety. Another example is Dewanjee et al., U.S. Pat. No. 7,785,522, which is hereby incorporated by reference in its entirety.

The mantle component is preferably composed of the inner mantle layer and the outer mantle layer. The mantle component preferably has a thickness ranging from 0.05 inch to 0.15 inch, and more preferably from 0.06 inch to 0.08 inch. The outer mantle layer is preferably composed of a blend of ionomer materials. One preferred embodiment comprises SURLYN 9150 material, SURLYN 8940 material, a SURLYN AD1022 material, and a masterbatch. The SURLYN 9150 material is preferably present in an amount ranging from 20 to 45 weight percent of the cover, and more preferably 30 to 40 weight percent. The SURLYN 8945 is preferably present in an amount ranging from 15 to 35 weight percent of the cover, more preferably 20 to 30 weight percent, and most preferably 26 weight percent. The SURLYN 9945 is preferably present in an amount ranging from 30 to 50 weight percent of the cover, more preferably 35 to 45 weight percent, and most preferably 41 weight percent. The SURLYN 8940 is preferably present in an amount ranging from 5 to 15 weight percent of the cover, more preferably 7 to 12 weight percent, and most preferably 10 weight percent.

SURLYN 8320, from DuPont, is a very-low modulus ethylene/methacrylic acid copolymer with partial neutralization of the acid groups with sodium ions. SURLYN 8945, also from DuPont, is a high acid ethylene/methacrylic acid copolymer with partial neutralization of the acid groups with sodium ions. SURLYN 9945, also from DuPont, is a high acid ethylene/methacrylic acid copolymer with partial neutralization of the acid groups with zinc ions. SURLYN 8940, also from DuPont, is an ethylene/methacrylic acid copolymer with partial neutralization of the acid groups with sodium ions.

The inner mantle layer is preferably composed of a blend of ionomers, preferably comprising a terpolymer and at least two high acid (greater than 18 weight percent) ionomers neutralized with sodium, zinc, magnesium, or other metal ions. The material for the inner mantle layer preferably has a Shore D plaque hardness ranging preferably from 35 to 77, more preferably from 36 to 44, a most preferably approximately 40. The thickness of the outer mantle layer preferably ranges from 0.025 inch to 0.050 inch, and is more preferably approximately 0.037 inch. The mass of an insert including the dual core and the inner mantle layer preferably ranges from 32 grams to 40 grams, more preferably from 34 to 38 grams, and is most preferably approximately 36 grams. The inner mantle layer is alternatively composed of a HPF material available from DuPont. Alternatively, the inner mantle layer 14b is composed of a material such as disclosed in Kennedy, III et al., U.S. Pat. No. 7,361,101 for a Golf Ball And Thermoplastic Material, which is hereby incorporated by reference in its entirety.

The outer mantle layer is preferably composed of a blend of ionomers, preferably comprising at least two high acid (greater than 18 weight percent) ionomers neutralized with sodium, zinc, or other metal ions. The blend of ionomers also preferably includes a masterbatch. The material of the outer mantle layer preferably has a Shore D plaque hardness ranging preferably from 55 to 75, more preferably from 65 to 71, and most preferably approximately 67. The thickness of the outer mantle layer preferably ranges from 0.025 inch to 0.040 inch, and is more preferably approximately 0.030 inch. The mass of the entire insert including the core, the inner mantle layer and the outer mantle layer preferably ranges from 38 grams to 43 grams, more preferably from 39 to 41 grams, and is most preferably approximately 41 grams.

In an alternative embodiment, the inner mantle layer is preferably composed of a blend of ionomers, preferably comprising at least two high acid (greater than 18 weight percent) ionomers neutralized with sodium, zinc, or other metal ions. The blend of ionomers also preferably includes a masterbatch. In this embodiment, the material of the inner mantle layer has a Shore D plaque hardness ranging preferably from 55 to 75, more preferably from 65 to 71, and most preferably approximately 67. The thickness of the outer mantle layer preferably ranges from 0.025 inch to 0.040 inch, and is more preferably approximately 0.030 inch. Also in this embodiment, the outer mantle layer 14b is composed of a blend of ionomers, preferably comprising a terpolymer and at least two high acid (greater than 18 weight percent) ionomers neutralized with sodium, zinc, magnesium, or other metal ions. In this embodiment, the material for the outer mantle layer 14b preferably has a Shore D plaque hardness ranging preferably from 35 to 77, more preferably from 36 to 44, a most preferably approximately 40. The thickness of the outer mantle layer preferably ranges from 0.025 inch to 0.100 inch, and more preferably ranges from 0.070 inch to 0.090 inch.

In other golf balls, the inner mantle layer is thicker than the outer mantle layer and the outer mantle layer is harder than the inner mantle layer, the inner mantle layer is composed of a blend of ionomers, preferably comprising a terpolymer and at least two high acid (greater than 18 weight percent) ionomers neutralized with sodium, zinc, magnesium, or other metal ions. In this embodiment, the material for the inner mantle layer has a Shore D plaque hardness ranging preferably from 30 to 77, more preferably from 30 to 50, and most preferably approximately 40. In this embodiment, the material for the outer mantle layer has a Shore D plaque hardness ranging preferably from 40 to 77, more preferably from 50 to 71, and most preferably approximately 67. In this embodiment, the thickness of the inner mantle layer preferably ranges from 0.030 inch to 0.090 inch, and the thickness of the outer mantle layer ranges from 0.025 inch to 0.070 inch.

Preferably the inner core has a diameter ranging from 0.75 inch to 1.20 inches, more preferably from 0.85 inch to 1.05 inch, and most preferably approximately 0.95 inch. Preferably the inner core 12a has a Shore D hardness ranging from 20 to 50, more preferably from 25 to 40, and most preferably approximately 35. Preferably the inner core is formed from a polybutadiene, zinc diacrylate, zinc oxide, zinc stearate, a peptizer and peroxide. Preferably the inner core has a mass ranging from 5 grams to 15 grams, 7 grams to 10 grams and most preferably approximately 8 grams.

Preferably the outer core has a diameter ranging from 1.25 inch to 1.55 inches, more preferably from 1.40 inch to 1.5 inch, and most preferably approximately 1.5 inch. Preferably the inner core has a Shore D surface hardness ranging from 40 to 65, more preferably from 50 to 60, and most preferably approximately 56. Preferably the inner core is formed from a polybutadiene, zinc diacrylate, zinc oxide, zinc stearate, a peptizer and peroxide. Preferably the combined inner core and outer core have a mass ranging from 25 grams to 35 grams, 30 grams to 34 grams and most preferably approximately 32 grams.

Preferably the inner core has a deflection of at least 0.230 inch under a load of 220 pounds, and the core has a deflection of at least 0.080 inch under a load of 200 pounds. As shown, a mass 50 is loaded onto an inner core and a core. As shown in FIGS. 6 and 7, the mass is 100 kilograms, approximately 220 pounds. Under a load of 100 kilograms, the inner core preferably has a deflection from 0.230 inch to 0.300 inch. Under a load of 100 kilograms, preferably the core has a deflection of 0.08 inch to 0.150 inch. Alternatively, the load is 200 pounds (approximately 90 kilograms), and the deflection of the core 12 is at least 0.080 inch. Further, a compressive deformation from a beginning load of 10 kilograms to an ending load of 130 kilograms for the inner core ranges from 4 millimeters to 7 millimeters and more preferably from 5 millimeters to 6.5 millimeters. The dual core deflection differential allows for low spin off the tee to provide greater distance, and high spin on approach shots.

In an alternative embodiment of the golf ball, the golf ball 10 comprises an inner core 12a, an intermediate core 12b, an outer core 12b, a mantle 14 and a cover 16. The golf ball 10 preferably has a diameter of at least 1.68 inches, a mass ranging from 45 grams to 47 grams, a COR of at least 0.79, a deformation under a 100 kilogram loading of at least 0.07 mm.

In one embodiment, the golf ball comprises a core, a mantle layer and a cover layer. The core comprises an inner core sphere, an intermediate core layer and an outer core layer. The inner core sphere comprises a polybutadiene material and has a diameter ranging from 0.875 inch to 1.4 inches. The intermediate core layer is composed of a highly neutralized ionomer and has a Shore D hardness less than 40. The outer core layer is composed of a highly neutralized ionomer and has a Shore D hardness less than 45. A thickness of the intermediate core layer is greater than a thickness of the outer core layer. The mantle layer is disposed over the core, comprises an ionomer material and has a Shore D hardness greater than 55. The cover layer is disposed over the mantle layer comprises a thermoplastic polyurethane material and has a Shore A hardness less than 100. The golf ball has a diameter of at least 1.68 inches. The mantle layer is harder than the outer core layer, the outer core layer is harder than the intermediate core layer, the intermediate core layer is harder than the inner core sphere, and the cover layer is softer than the mantle layer.

In another golf ball, the golf ball 10 has a multi-layer core and multi-layer mantle. The golf ball includes a core, a mantle component and a cover layer. The core comprises an inner core sphere, an intermediate core layer and an outer core layer. The inner core sphere comprises a polybutadiene material and has a diameter ranging from 0.875 inch to 1.4 inches. The intermediate core layer is composed of a highly neutralized ionomer and has a Shore D hardness less than 40. The outer core layer is composed of a highly neutralized ionomer and has a Shore D hardness less than 45. A thickness of the intermediate core layer is greater than a thickness of the outer core layer 12c. The inner mantle layer is disposed over the core, comprises an ionomer material and has a Shore D hardness greater than 55. The outer mantle layer is disposed over the inner mantle layer, comprises an ionomer material and has a Shore D hardness greater than 60. The cover layer is disposed over the mantle component, comprises a thermoplastic polyurethane material and has a Shore A hardness less than 100. The golf ball has a diameter of at least 1.68 inches. The outer mantle layer is harder than the inner mantle layer, the inner mantle layer is harder than the outer core layer, the outer core layer is harder than the intermediate core layer, the intermediate core layer is harder than the inner core sphere, and the cover layer is softer than the outer mantle layer.

In a particularly preferred embodiment of the invention, the golf ball preferably has an aerodynamic pattern such as disclosed in Simonds et al., U.S. Pat. No. 7,419,443 for a Low Volume Cover For A Golf Ball, which is hereby incorporated by reference in its entirety. Alternatively, the golf ball has an aerodynamic pattern such as disclosed in Simonds et al., U.S. Pat. No. 7,338,392 for An Aerodynamic Surface Geometry For A Golf Ball, which is hereby incorporated by reference in its entirety.

Various aspects of the present invention golf balls have been described in terms of certain tests or measuring procedures. These are described in greater detail as follows.

As used herein, "Shore D hardness" of the golf ball layers is measured generally in accordance with ASTM D-2240 type D, except the measurements may be made on the curved surface of a component of the golf ball, rather than on a plaque. If measured on the ball, the measurement will indicate that the measurement was made on the ball. In referring to a hardness of a material of a layer of the golf ball, the measurement will be made on a plaque in accordance with ASTM D-2240. Furthermore, the Shore D hardness of the cover is measured while the cover remains over the mantles and cores. When a hardness measurement is made on the golf ball, the Shore D hardness is preferably measured at a land area of the cover.

As used herein, "Shore A hardness" of a cover is measured generally in accordance with ASTM D-2240 type A, except the measurements may be made on the curved surface of a component of the golf ball, rather than on a plaque. If measured on the ball, the measurement will indicate that the measurement was made on the ball. In referring to a hardness of a material of a layer of the golf ball, the measurement will be made on a plaque in accordance with ASTM D-2240. Furthermore, the Shore A hardness of the cover is measured while the cover remains over the mantles and cores. When a hardness measurement is made on the golf ball, Shore A hardness is preferably measured at a land area of the cover The resilience or coefficient of restitution (COR) of a golf ball is the constant "e," which is the ratio of the relative velocity of an elastic sphere after direct impact to that before impact. As a result, the COR ("e") can vary from 0 to 1, with 1 being equivalent to a perfectly or completely elastic collision and 0 being equivalent to a perfectly or completely inelastic collision.

COR, along with additional factors such as club head speed, club head mass, ball weight, ball size and density, spin rate, angle of trajectory and surface configuration as well as environmental conditions (e.g. temperature, moisture, atmospheric pressure, wind, etc.) generally determine the distance a ball will travel when hit. Along this line, the distance a golf ball will travel under controlled environmental conditions is a function of the speed and mass of the club and size, density and resilience (COR) of the ball and other factors. The initial velocity of the club, the mass of the club and the angle of the ball's departure are essentially provided by the golfer upon striking. Since club head speed, club head mass, the angle of trajectory and environmental conditions are not determinants controllable by golf ball producers and the ball size and weight are set by the U.S.G.A., these are not factors of concern among golf ball manufacturers. The factors or determinants of interest with respect to improved distance are generally the COR and the surface configuration of the ball.

The coefficient of restitution is the ratio of the outgoing velocity to the incoming velocity. In the examples of this application, the coefficient of restitution of a golf ball was measured by propelling a ball horizontally at a speed of 125+/−5 feet per second (fps) and corrected to 125 fps against a generally vertical, hard, flat steel plate and measuring the ball's incoming and outgoing velocity electronically. Speeds were measured with a pair of ballistic screens, which provide a timing pulse when an object passes through them. The screens were separated by 36 inches and are located 25.25 inches and 61.25 inches from the rebound wall. The ball speed was measured by timing the pulses from screen 1 to screen 2 on the way into the rebound wall (as the average speed of the ball over 36 inches), and then the exit speed was timed from screen 2 to screen 1 over the same distance. The rebound wall was tilted 2 degrees from a vertical plane to allow the ball to rebound slightly downward in order to miss the edge of the cannon that fired it. The rebound wall is solid steel.

As indicated above, the incoming speed should be 125±5 fps but corrected to 125 fps. The correlation between COR and forward or incoming speed has been studied and a correction has been made over the ±5 fps range so that the COR is reported as if the ball had an incoming speed of exactly 125.0 fps.

The measurements for deflection, compression, hardness, and the like are preferably performed on a finished golf ball as opposed to performing the measurement on each layer during manufacturing.

Preferably, in a five layer golf ball comprising an inner core, an outer core, an inner mantle layer, an outer mantle layer and a cover, the hardness/compression of layers involve an inner core with the greatest deflection (lowest hardness), an outer core (combined with the inner core) with a deflection less than the inner core, an inner mantle layer with a hardness less than the hardness of the combined outer core and inner core, an outer mantle layer with the hardness layer of the golf ball, and a cover with a hardness less than the hardness of the outer mantle layer. These measurements are preferably made on a finished golf ball that has been torn down for the measurements.

Preferably the inner mantle layer is thicker than the outer mantle layer or the cover layer. The dual core and dual mantle golf ball creates an optimized velocity-initial velocity ratio (Vi/IV), and allows for spin manipulation. The dual core provides for increased core compression differential resulting in a high spin for short game shots and a low spin for driver shots. A discussion of the USGA initial velocity test is disclosed in Yagley et al., U.S. Pat. No. 6,595,872 for a Golf Ball With High Coefficient Of Restitution, which is hereby incorporated by reference in its entirety. Another example is Bartels et al., U.S. Pat. No. 6,648,775 for a Golf Ball With High Coefficient Of Restitution, which is hereby incorporated by reference in its entirety.

Crast et al., U.S. Pat. No. 6,632,877, for a Dual Curable Coating, is hereby incorporated by reference in its entirety.

Skrabski et al., U.S. Pat. No. 6,544,337, for a Golf ball Painting System, is hereby incorporated by reference in its entirety.

Crast et al., U.S. Pat. No. 6,365,679, for a Two component polyurethane clear coat for golf balls, is hereby incorporated by reference in its entirety.

Crast et al., U.S. Pat. No. 6,165,564, for a UV Clearable Clear Coat For Golf Balls, is hereby incorporated by reference in its entirety.

Skrabski et al., U.S. Pat. No. 6,319,563, for a Golf ball Painting Method, is hereby incorporated by reference in its entirety.

Bartels, U.S. Pat. No. 9,278,260, for a Low Compression Three-Piece Golf Ball With An Aerodynamic Drag Rise At High Speeds, is hereby incorporated by reference in its entirety.

Chavan et al, U.S. Pat. No. 9,789,366, for a Graphene Core For A Golf Ball, is hereby incorporated by reference in its entirety.

Chavan et al, U.S. patent application Ser. No. 15/705,011, filed on Sep. 14, 2017, for a Graphene Core For A Golf Ball, is hereby incorporated by reference in its entirety.

Chavan et al, U.S. patent application Ser. No. 15/729,231, filed on Oct. 10, 2017, for a Graphene And Nanotube Reinforced Golf Ball, is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modifications and substitutions of equivalents may be made therein without departing from the spirit and scope of this invention which is intended to be unlimited by the foregoing except as may appear in the following appended claims. Therefore, the embodiments of the invention in which an exclusive property or privilege is claimed are defined in the following appended claims.

We claim as our invention the following:

1. A machine for determining concentricity of a multiple layer golf ball, the machine comprising:
   an x-ray source;
   a digital detector;
   a static fixture within a measurement region;
   wherein the machine is configured to average a first plurality of images of the full cross-sectional view of the golf ball using the x-ray source and the digital detector into a single first image of a full cross-sectional view of the golf ball;
   wherein the machine is configured to calculate Y,Z center coordinates of a best fit diameter or ellipse of an inner edge layer and an outer edge layer of a specific layer of the multiple layer golf ball using the single first image of the full cross-sectional view of the golf ball;
   wherein the machine is configured to average a second plurality of images of the full cross-sectional view of the golf ball in a new orientation using the x-ray source and the digital detector into a second single image of the full cross-sectional view of the golf ball;
   wherein the machine is configured to calculate X,Z center coordinates of a best fit diameter or ellipse of the inner edge layer and outer edge layer of the specific layer of the multiple layer golf ball; and
   wherein the machine is configured to compare the X, Z and Y,Z center coordinates of the specific layer to determine the concentricity of the specific layer within an outer layer of the multiple layer golf ball.

2. The machine according to claim 1 wherein the plurality of images range from 2 to 24 and a single image is derived by averaging a plurality of images.

3. The machine according to claim 1 wherein the concentricity of the inner and outer edges are calculated using Euclidean distances.

4. The machine according to claim 1 wherein the machine is configured to evaluate the golf ball against a predetermined criteria.

5. The machine according to claim 1 wherein the machine is configured to sort the golf ball according to the evaluation.

* * * * *